(12) United States Patent
Gillies

(10) Patent No.: US 10,017,579 B2
(45) Date of Patent: *Jul. 10, 2018

(54) ANTI-CANCER ANTIBODIES WITH REDUCED COMPLEMENT FIXATION

(71) Applicant: Merck Patent GmbH, Darmstadt (DE)

(72) Inventor: Stephen D. Gillies, Carlisle, MA (US)

(73) Assignee: Meck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/483,698

(22) Filed: Apr. 10, 2017

(65) Prior Publication Data

US 2017/0210817 A1 Jul. 27, 2017

Related U.S. Application Data

(60) Division of application No. 14/478,753, filed on Sep. 5, 2014, now Pat. No. 9,617,349, which is a continuation of application No. 12/209,935, filed on Sep. 12, 2008, now Pat. No. 8,835,606, which is a continuation of application No. 11/040,071, filed on Jan. 21, 2005, now Pat. No. 7,432,357.

(60) Provisional application No. 60/538,348, filed on Jan. 22, 2004.

(51) Int. Cl.
| | |
|---|---|
| A61K 39/395 | (2006.01) |
| C07K 16/30 | (2006.01) |
| C07K 16/44 | (2006.01) |
| A61K 39/00 | (2006.01) |

(52) U.S. Cl.
CPC .......... *C07K 16/3084* (2013.01); *C07K 16/44* (2013.01); *A61K 2039/505* (2013.01); *C07K 2317/52* (2013.01); *C07K 2317/522* (2013.01); *C07K 2317/56* (2013.01); *C07K 2317/732* (2013.01); *C07K 2317/734* (2013.01)

(58) Field of Classification Search
None
See application file for complete search history.

(56) References Cited

U.S. PATENT DOCUMENTS

| | | |
|---|---|---|
| 4,196,265 A | 4/1980 | Koprowski et al. |
| 4,676,980 A | 6/1987 | Segal et al. |
| 4,816,567 A | 3/1989 | Cabilly et al. |
| 4,946,778 A | 8/1990 | Ladner et al. |
| 4,975,369 A | 12/1990 | Beavers et al. |
| 5,082,658 A | 1/1992 | Palladino |
| 5,091,513 A | 2/1992 | Huston et al. |
| 5,114,711 A | 5/1992 | Bell et al. |
| 5,116,964 A | 5/1992 | Capon et al. |
| 5,225,538 A | 7/1993 | Capon et al. |
| 5,225,539 A | 7/1993 | Winter |
| 5,258,498 A | 11/1993 | Huston et al. |
| 5,314,995 A | 5/1994 | Fell, Jr. et al. |
| 5,359,035 A | 10/1994 | Habermann |
| 5,399,346 A | 3/1995 | Anderson et al. |
| 5,428,130 A | 6/1995 | Capon et al. |
| 5,514,582 A | 5/1996 | Capon et al. |
| 5,541,087 A | 7/1996 | Lo et al. |
| 5,585,089 A | 12/1996 | Queen et al. |
| 5,601,819 A | 2/1997 | Wong et al. |
| 5,624,821 A | 4/1997 | Winter et al. |
| 5,645,835 A | 7/1997 | Fell, Jr. et al. |
| 5,650,150 A | 7/1997 | Gillies |
| 5,677,425 A | 10/1997 | Bodmer et al. |
| 5,679,543 A | 10/1997 | Lawlis |
| 5,712,120 A | 1/1998 | Rodriguez et al. |
| 5,723,125 A | 3/1998 | Chang et al. |
| 5,726,044 A | 3/1998 | Lo et al. |
| 5,770,195 A | 6/1998 | Hudziak et al. |
| 5,807,715 A | 9/1998 | Morrison et al. |
| 5,827,516 A | 10/1998 | Urban et al. |
| 5,827,703 A | 10/1998 | Debs et al. |
| 5,837,821 A | 11/1998 | Wu |
| 5,843,423 A | 12/1998 | Lyman et al. |
| 5,888,773 A | 3/1999 | Jost et al. |
| 5,908,626 A | 6/1999 | Chang et al. |
| 6,100,387 A | 8/2000 | Herrmann et al. |
| 6,277,375 B1 | 8/2001 | Ward |
| 6,281,010 B1 | 8/2001 | Gao et al. |
| 6,284,536 B1 | 9/2001 | Morrison et al. |
| 6,291,158 B1 | 9/2001 | Winter et al. |
| 6,335,176 B1 | 1/2002 | Inglese et al. |

(Continued)

FOREIGN PATENT DOCUMENTS

| | | |
|---|---|---|
| AU | 21725/88 A | 3/1989 |
| EP | 0294703 A2 | 12/1988 |

(Continued)

OTHER PUBLICATIONS

Thommesen et al (Molecular immunology, 2003, 37:995-1004) (Year: 2003).*
Abaza et al., (1992), "Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin," J Prot Chem, 11(5):433-44.
Adkins et al., (1998), "Edrecolomab (Monoclonal Antibody 17-1A)," Drugs, 56(4):619-26.
Anderson et al., (1980), "Characterization of the Fc Receptor for IgG on a Human Macrophage Cell Line U937," Immunology, 125(6):2735-41.
Angal et al., (1993), "A Single Amino Acid Substitution Abolishes the Heterogeneity of Chimeric Mouse/Human (IgG4) Antibody," Mol Immunol, 30(1):105-8.

(Continued)

*Primary Examiner* — Laura B Goddard
*Assistant Examiner* — Meera Natarajan
(74) *Attorney, Agent, or Firm* — Goodwin Procter LLP

(57) ABSTRACT

The invention provides modified antibodies directed against GD2 that have diminished complement fixation relative to antibody-dependent, cell-mediated cytotoxicity, which is maintained. The modified antibodies of the invention may be used in the treatment of tumors such as neuroblastoma, glioblastoma, melanoma, small-cell lung carcinoma, B-cell lymphoma, renal carcinoma, retinoblastoma, and other cancers of neuroectodermal origin.

15 Claims, 11 Drawing Sheets

(56) References Cited

U.S. PATENT DOCUMENTS

| | | |
|---|---|---|
| 6,410,008 B1 | 6/2002 | Strom et al. |
| 6,475,717 B1 | 11/2002 | Enssle et al. |
| 6,617,135 B1 | 9/2003 | Gillies et al. |
| 6,627,615 B1 | 9/2003 | Debs et al. |
| 6,646,113 B1 | 11/2003 | Dreyfuss et al. |
| 6,838,260 B2 | 1/2005 | Gillies et al. |
| 6,972,323 B1 | 12/2005 | Serizawa et al. |
| 7,183,387 B1 | 2/2007 | Presta |
| 7,432,357 B2 | 10/2008 | Gillies |
| 8,835,606 B2 | 9/2014 | Gillies |
| 2002/0037558 A1 | 3/2002 | Lo et al. |
| 2002/0081664 A1 | 6/2002 | Lo et al. |
| 2002/0114781 A1 | 8/2002 | Strom et al. |
| 2002/0146388 A1 | 10/2002 | Gillies |
| 2002/0147311 A1 | 10/2002 | Gillies et al. |
| 2002/0193570 A1 | 12/2002 | Gillies et al. |
| 2003/0003529 A1 | 1/2003 | Bayer |
| 2003/0044423 A1 | 3/2003 | Gillies et al. |
| 2003/0049227 A1 | 3/2003 | Gillies et al. |
| 2003/0103963 A1 | 6/2003 | Cheung |
| 2003/0105294 A1 | 6/2003 | Gillies et al. |
| 2003/0139365 A1 | 7/2003 | Lo et al. |
| 2003/0139575 A1 | 7/2003 | Gillies |
| 2003/0157054 A1 | 8/2003 | Gillies et al. |
| 2003/0166163 A1 | 9/2003 | Gillies |
| 2003/0166868 A1 | 9/2003 | Presta et al. |
| 2003/0166877 A1 | 9/2003 | Gillies et al. |
| 2004/0033210 A1 | 2/2004 | Gillies |
| 2004/0043457 A1 | 3/2004 | Schumacher et al. |
| 2004/0053366 A1 | 3/2004 | Lo et al. |
| 2004/0072299 A1 | 4/2004 | Gillies et al. |
| 2004/0082039 A1 | 4/2004 | Gillies et al. |
| 2004/0180035 A1 | 9/2004 | Gillies |
| 2004/0180386 A1 | 9/2004 | Carr et al. |
| 2004/0203100 A1 | 10/2004 | Gillies et al. |
| 2005/0069521 A1 | 3/2005 | Gillies et al. |

FOREIGN PATENT DOCUMENTS

| | | |
|---|---|---|
| EP | 0308936 A2 | 3/1989 |
| EP | 0314317 A1 | 5/1989 |
| EP | 0318554 A1 | 6/1989 |
| EP | 0326120 A2 | 8/1989 |
| EP | 0344134 A2 | 11/1989 |
| EP | 0428596 A1 | 5/1991 |
| EP | 0439095 A2 | 7/1991 |
| EP | 0511747 A1 | 11/1992 |
| EP | 0519596 A1 | 12/1992 |
| EP | 0601043 A1 | 6/1994 |
| EP | 0699755 A2 | 3/1996 |
| EP | 1088888 A1 | 4/2001 |
| EP | 1176195 A1 | 1/2002 |
| GB | 2188638 A | 10/1987 |
| WO | WO-1986/001533 A1 | 3/1986 |
| WO | WO-1988/009344 A1 | 12/1988 |
| WO | WO-1989/009620 A1 | 10/1989 |
| WO | WO-1991/004329 A1 | 4/1991 |
| WO | WO-1991/008298 A2 | 6/1991 |
| WO | WO-1991/013166 A1 | 9/1991 |
| WO | WO-1992/002240 A2 | 2/1992 |
| WO | WO-1992/008495 A1 | 5/1992 |
| WO | WO-1992/008801 A1 | 5/1992 |
| WO | WO-1992/010755 A1 | 6/1992 |
| WO | WO-1992/016562 A1 | 10/1992 |
| WO | WO-1993/003157 A1 | 2/1993 |
| WO | WO-1994/025609 A1 | 11/1994 |
| WO | WO-1995/005468 A1 | 2/1995 |
| WO | WO-1996/008570 A1 | 3/1996 |
| WO | WO-1997/000317 A1 | 1/1997 |
| WO | WO-1997/024137 A1 | 7/1997 |
| WO | WO-1997/030089 A1 | 8/1997 |
| WO | WO-1997/034631 A1 | 9/1997 |
| WO | WO-1998/052976 A1 | 11/1998 |
| WO | WO-1998/059244 A1 | 12/1998 |
| WO | WO-1999/003887 A1 | 1/1999 |
| WO | WO-1999/029732 A2 | 6/1999 |
| WO | WO-2000/001822 A1 | 1/2000 |
| WO | WO-2000/034317 A2 | 6/2000 |
| WO | WO-2002/079232 A2 | 10/2002 |

OTHER PUBLICATIONS

Baici et al., (1980), "Kinetics of the Different Susceptibilities of the Four Human Immunoglobulin G Subclasses to Proteolysis by Human Lysosomal Elastase," Scand J Immunol, 12(1):41-50.

Batova et al., (1999), "The Ch14.18-GM-CSF Fusion Protein is Effective at Mediating Antibody-Dependent Cellular Cytotoxicity and Complement-Dependent Cytotoxicity in vitro," Clin Cancer Res, 5:4259-63.

Batra et al., (1993), "Insertion of Constant Region Domains of Human IgG1 into CD4-PE40 Increases Its Plasma Half-Life," Mol Immunol, 30(4):379-86.

Becker et al., (1996), "An Antibody-Interleukin 2 Fusion Protein Overcomes Tumor Heterogeneity by Induction of a Cellular Immune Response," Proc Natl Acad Sci USA, 93:7826-31.

Becker et al., (1996), "Eradication of Human Hepatic and Pulmonary Melanoma Metastases in SCID Mice by Antibody-Interleukin 2 Fusion Proteins," Proc Natl Acad Sci USA, 93:2702-7.

Becker et al., (1996), "Long-Lived and Transferable Tumor Immunity in Mice after Targeted Interleukin-2 Therapy," J Clin Invest, 98(12):2801-4.

Becker et al., (1996), "T Cell-Mediated Eradication of Murine Metastatic Melanoma Induced by Targeted Interleukin-2 Therapy," J Exp Med, 183(50):2361-6.

Beutler et al., (1988), "Tumor Necrosis, Cachexia, Shock, and Inflammation: A Common Mediator," Ann Rev Biochem, 57:505-18.

Bitonti et al. (2004), "Pulmonary Delivery of an Erythropoietin Fc Fusion Protein in Non-Human Primates Through an Immunoglobulin Transport Pathway," Proc Natl Acad Sci USA, 101(26):9763-8.

Bjorn et al., (1985), "Evaluation of Monoclonal Antibodies for the Development of Breast Cancer Immunotoxins," Cancer Res, 45:1214-21.

Boulianne et al., (1984), "Production of Functional Chimaeric Mouse/Human Antibody," Nature, 312:643-6.

Bourgois et al., (1974), "Determination of the Primary Structure of a Mouse IgG2a Immunoglobulin: Amino-Acid Sequence of the Fc Fragment: Implications for the Evolution of Immunoglobulin Structure and Function," Eur J Biochem, 43:423-35.

Brambell et al., (1964), "A Theoretical Model of γ-Globulin Catabolism," Nature, 203:1352-5.

Brekke et al., (1994), "Human IgG Isotype-Specific Amino Acid Residues Affecting Complement-Mediated Cell Lysis and Phagocytosis," Eur J Immunol, 24:2542-7.

Bubenik et al., (1995), "Interleukin-2 Gene Therapy of Residual EL-4 Leukaemia Potentiates the Effect of Cyclophosphamide Pretreatment," J Cancer Res Clin Oncol, 121:39-43.

Burgess et al., (1990), "Possible Dissociation of the Heparin-Binding and Mitogenic Activities of Heparin-Binding (Acidic Fibroblast) Growth Factor-1 from Its Receptor-Binding Activities by Site-Directed Mutagenesis of a Single Lysine Residue,"J Cell Biol, 111:2129-38.

Canfield et al., (1991), "The Binding Affinity of Human IgG for its High Affinity Fc Receptor is Determined by Multiple Amino Acids in the CH2 Domain and is Modulated by the Hinge Region," J Exp Med, 173(6):1483-91.

Capon et al., (1989), "Designing CD4 Immunoadhesins for AIDS Therapy," Nature, 337:525-31.

Caton et al., (1986), "Structural and Functional Implications of a Restricted Antibody Response to a Defined Antigenic Region on the Influenza Virus Hemagglutinin," EMBO J, 5(7):1577-87.

Chan et al., (1992), "Mechanisms of IFN-γ Induction by Natural Killer Cell Stimulatory Factor (NKSF/IL-12). Role of Transcription and mRNA Stability in the Synergistic Interaction Between NKSF and IL-2," Immunology, 148:92-8.

(56) References Cited

OTHER PUBLICATIONS

Chapman et al., (1994), "Mapping Effector Functions of a Monoclonal Antibody to GD3 by Characterization of a Mouse-Human Chimeric Antibody," Cancer Immuno Immunother, 39:198-204.
Chappel et al., (1991), "Identification of the Fc γ Receptor Class I Binding Site in Human IgG Through Use of Recombinant IgG1/IgG2 Hybrid and Point-Mutated Antibodies," Proc Natl Acad Sci USA, 88:(20):9036-40.
Chaudhary et al., (1988), "Selective Killing of HIV-Infected Cells by Recombinant Human CD4-Pseudomonas Exotoxin Hybrid Protein," Nature, 335:370-2.
Chaudhary et al., (1989), "A Recombinant Immunotoxin Consisting of Two Antibody Variable Domains Fused to Pseudomonas Exotoxin," Nature, 339:394-7.
Cheon et al., (1994), "High-Affinity Binding Sites for Related Fibroblast Growth Factor Ligands Reside Within Different Receptor Immunoglobulin-Like Domains," Proc Natl Acad Sci USA, 91:989-93.
Cirulli et al., (1998), "KSA Antigen Ep-CAM Mediates Cell-Cell Adhesion of Pancreatic Epithelial Cells: Morphoregulatory Roles in Pancreatic Islet Development," J Cell Biol, 140:1519-34.
Cohen et al., (1998), "An Artificial Cell-Cycle Inhibitor Isolated from a Combinatorial Library," Proc Natl Acad Sci USA, 95:14272-7.
Cole et al., (1997), "Human IgG2 Variants of Chimeric Anti-CD3 are Nonmitogenic to T Cells," Immunology, 159:3613-21.
Colman, (1994), "Effects of Amino Acid Sequence Changes on Antibody-Antigen Interactions," Res Immunol, 145(1):33-6.
Connor et al., (2004), "Ex vivo Evaluation of Anti-EpCAM Immunocytokine huKS-IL2 in Ovarian Cancer," Immunotherapy, 27:211-9.
Davis et al., (2003), "Immunocytokines: Amplification of Anti-Cancer Immunity," Cancer Immunol. Immunother., 52:297-308.
De la Salle et al., (1996), "FcγR on Human Dendritic Cells," *Human IgG Fc Receptors*, (1$^{st}$ Ed, 1996), JGJ van de Winkel and PJA Capel (Eds), R.G. Landes Company, Austin, TX (Pub), pp. 39-55.
Dolman et al., (1998), "Suppression of Human Prostate Carcinoma Metastases in Severe Combined Immunodeficient Mice by Interleukin 2 Immunocytokine Therapy," Clin. Cancer Research., 4(10):2551-7.
Dorai et al., (1991), "Aglycosylated Chimeric Mouse/Human IgG1 Antibody Retains Some Effector Function," Hybridoma, 10(2):211-7.
Dorai et al., (1992), "Role of Inter-Heavy and Light Chain Disulfide Bonds in the Effector Functions of Human IgG1," Molec Immunol, 29(12):1487-91.
Duncan et al., (1988), "The Binding Site for C1q on IgG," Nature, 332:738-40.
Ellison et al., (1982), "The Nucleotide Sequence of a Human Immunoglobulin Cγ1 Gene," Nuc Acids Res., 10:4071-9.
Fell et al., (1991), "Genetic Construction and Characterization of a Fusion Protein Consisting of a Chimeric F(ab') with Specificity for Carcinomas and Human IL-2," Immunology, 146(7):2446-52.
Fell et al., (1992), "Chimeric L6 Anti-Tumor Antibody: Genomic Construction, Expression, and Characterization of the Antigen Binding Site," J Biol Chem, 267:15552-8.
Frost et al. (1997), "A Phase I/IB Trial of Murine Monoclonal Anti-GD2 Antibody 14.G2a Plus Interleukin-2 in Children with Refractory Neuroblastoma," Cancer, 80(2):317-33.
Gan et al., (1999), "Specific Enzyme-Linked Immunosorbent Assays for Quantitation of Antibody-Cytokine Fusion Proteins," Clinical and Diagnostic Laboratory Immunology, 6(2):236-42.
Gasson et al., (1984), "Purified Human Granulocyte Macrophage Colony-Stimulating Factor: Direct Action on Neutrophils," Science, 226:1339-42.
Ghetie et al., (1997), "FcRn: The MHC Class I-Related Receptor that is More Than an IgG Transporter," Immunol Today, 18(12):592-8.

Gillies et al., (1989), "Expression of Human Anti-Tetanus Toxoid Antibody in Transfected Murine Myeloma Cells," Bio/Technology, 7:799-804.
Gillies et al., (1989), "High-Level Expression of Chimeric Antibodies Using Adapted cDNA Variable Region Cassettes," J Immunol Meth, 125:191-202.
Gillies et al., (1990), "Antigen Binding and Biological Activities of Engineered Mutant Chimeric Antibodies with Human Tumor Specificities," Hum Antibod Hybridomas, 1(1):47-54.
Gillies et al., (1991), "Expression of Genetically Engineered Immunoconjugates of Lymphotoxin and a Chimeric Anti-Ganglioside GD2 Antibody," Hybridoma., 10(3):347-56.
Gillies et al., (1991), "Targeting Human Cytotoxic T Lymphocytes to Kill Heterologous Epidermal Growth Factor Receptor-Bearing Tumor Cells: Tumor-Infiltrating Lymphocyte/Hormone Receptor/Recombinant Antibody," Immunology, 146(3):1067-71.
Gillies et al., (1992), "Antibody-Targeted Interleukin 2 Stimulates T-Cell Killing of Autologous Tumor Cells," Proc. Natl. Acad. Sci. USA, 89:1428-32.
Gillies et al., (1993), "Biological Activity and in vivo Clearance of Antitumor Antibody/Cytokine Fusion Proteins," Bioconj Chem., 4(3):230-5.
Gillies et al., (1998), "Antibody-IL-12 Fusion Proteins are Effective in SCID Mouse Models of Prostate and Colon Carcinoma Metastases," Immunology, 160:6195-203.
Gillies et al., (1999), "Improving the Efficacy of Antibody-Interleukin 2 Fusion Proteins by Reducing Their Interaction with Fc Receptors," Cancer Res, 59:2159-66.
Gillies et al., (2002), "Bi-Functional Cytokine Fusion Proteins for Gene Therapy and Antibody-Targeted Treatment of Cancer," Cancer Immunol Immunother, 51(8):449-60.
Gillies et al., (2002), "Improved Circulating Half-Life and Efficacy of an Antibody-Interleukin 2 Immunocytokine Based on Reduced Intracellular Proteolysis," Clin Cancer Res, 8(1):210-6.
Goeddel et al., (1986), "Tumor Necrosis Factors: Gene Structure and Biological Activities," Cold Spring Harb Symp Ouant Biol, 51:597-609.
Gren et al., (1983), "A New Type of Leukocytic Interferon," Dokl. Akad. Nauk. SSSR., 269(4):986-90 (Translation).
Grimaldi et al., (1989), "The t(5;14) Chromosomal Translocation in a Case of Acute Lymphocytic Leukemia Joins the Interleukin-3 Gene to the Immunoglobulin Heavy Chain Gene," Blood, 73(8):2081-5.
Gurewich et al., (1988), "Characterization of the Intrinsic Fibrinolytic Properties of Pro-Urokinase Through a Study of Plasmin-Resistant Mutant Forms Produced by Site-Specific Mutagenesis of Lysine," J Clin Invest, 82:1956-62.
Guyre et al., (1997), "Increased Potency of Fc-Receptor-Targeted Antigens," Cancer Immunol Immunother, 45:146-8.
Halin et al., (2002), "Enhancement of the Antitumor Activity of Interleukin-12 by Targeted Delivery to Neovasculature," Nat Biotechnol, 20:264-9.
Handgretinger et al., (1995), "A Phase 1 study of Human/Mouse Chimeric Anti-Ganglioside GD2 Antibody ch14.18 in Patients with Neuroblastoma," Eur J Cancer, 31A(2):7.
Hank et al., (1996), "Activation of Human Effector Cells by a Tumor Reactive Recombinant Anti-Ganglioside GD2 Interleukin-2 Fusion Protein (ch14.18-IL2)," Clin Cancer Res, 2(12):1951-9.
Hank et al., (2003), "Determination of Peak Serum Levels and Immune Response to the Humanized Anti-Ganglioside Antibody-Interleukin-2 Immunocytokine," vol. 85: Novel Anticancer Drug Protocols in *Methods in Molecular Medicine* series, JK Buolamwini and AA Adjei, (Eds), Humana Press Inc., Totowana, NJ, (Pub) pp. 123-131.
Haraguchi, (1994), "Isolation of GD3 Synthase Gene by Expression Cloning of GM3 α-2,8-sialyltransferase cDNA Using Anti-GD2 Monoclonal Antibody," Proc Natl Acad Sci USA, 91(22):10455-9.
Harris et al., (1993), "Therapeutic Antibodies—the Coming of Age," Trends Biotech, 11:42-4.
Harris, (1995), "Processing of C-Terminal Lysine and Arginine Residues of Proteins Isolated from Mammalian Cell Culture," J Chromatography A, 705:129-34.

(56) References Cited

OTHER PUBLICATIONS

Harvill et al., (1995), "An IgG3-IL2 Fusion Protein Activates Complement, Binds Fcγ RI, Generates LAK Activity and Shows Enhanced Binding to the High Affinity IL-2R," Immunotechnology, 1:95-105.
Harvill et al., (1996), "In vivo Properties of an IgG3-IL-2 Fusion Protein: A General Strategy for Immune Potentiation," Immunology, 157(7):3165-70.
He et al., (1998), "Humanization and Pharmacokinetics of a Monoclonal Antibody with Specificity for Both E-and P-Selectin," Immunology, 160:1029-35.
Hellstrom et al., (1986), "Antitumor Effects of L6, and IgG2a Antibody that Reacts with Most Human Carcinomas," Proc Natl Acad Sci USA, 83:7059-63.
Henkart, (1985), "Mechanism of Lymphocyte-Mediated Cytotoxicity," Ann Rev Immunol, 3:31-58.
Herrmann et al., (1989), "Hematopoietic Responses With Advanced Malignancy Treated With Recombinant Human Granulocyte-Macrophage Colony-Stimulating Factor," J Clin Oncol 7(2):159-67.
Hezareh et al., (2001), "Effector Function Activities of a Panel of Mutants of a Broadly Neutralizing Antibody against Human Immunodeficiency Virus Type 1," Virology, 75(24):12161-8.
Holden et al., (2001), "Augmentation of Anti-Tumor Activity of KS-IL2 Immunocytokine with Chemotherapeutic Agents," Proceedings of the American Association for Cancer Research, 42:683, Abstract No. 3675 (XP-002195344).
Holden et al., (2001), "Augmentation of Antitumor Activity of an Antibody-Interleukin 2 Immunocytokine with Chemotherapeutic Agents," Clinical Cancer Research, 7:2862-9.
Hornick et al., (1999), "Pretreatment with a Monoclonal Antibody/Interleukin-2 Fusion Protein Directed Against DNA Enhances the Delivery of Therapeutic Molecules to Solid Tumors," Clin Cancer Res, 5:51-60.
Huck et al., (1986), "Sequence of a Human Immunoglobulin Gamma 3 Heavy Chain Constant Region Gene: Comparison With the Other Human Cγ. genes," Nucl Acids Res, 14(4):1779-89.
Hulett et al., (1994), "Molecular Basis of Fc Receptor Function," Adv Immunol, 57:1127.
Hurn et al., (1980), "Production of Reagent Antibodies," Meth Enzymol, 70:104-42.
Huston et al., (1988), "Protein Engineering of Antibody Binding Sites: Recovery of Specific Activity in an Anti-Digoxin Single-Chain Fv Analogue Produced in *Escherichia coli*," Proc Natl Acad Sci USA, 85:5879-83.
Idusogie et al., (2000), "Mapping of the C1q Binding Site on Rituxan, A Chimeric Antibody with a Human IgG1 Fc," Immunology, 164:4178-84.
*Illustrated Dictionary of Immunology*, (1st Ed, 2009), JM Cruse (Ed), CRC Press, New York, NY (Pub), pp. 156-158.
Imboden et al., (2001), "The Level of MHC Class I Expression on Murine Adenocarcinoma Can Change the Antitumor Effector Mechanism of Immunocytokine Therapy," Cancer Res, 61(4):1500-7.
International Search Report for International Application No. PCT/EP2005/000428, dated Oct. 10, 2005 (3 pages).
Isaacs et al., (1998), "Therapy with Monoclonal Antibodies. II. The Contribution of Fcγ Receptor Binding and the Influence of CH1 and CH3 Domains on in vivo Effector Funcion," Immunology, 161:3862-9.
Isenman et al., (1975), "The Structure and Function of Immunoglobulin Domains: II. The Importance of Interchain Disulfide Bonds and the Possible Role of Molecular Flexibility in the Interaction between Immunoglobulin G and Complement," Immunology, 114(6):1726-9.
J Cruse and R Lewis, "Chapter 10: Cytokines," *Atlas of Immunology*, (2nd Ed, 2003), CRC Press LLC, Boca Raton, FL and Springer-Verlag gmbH & Co KCi, Heidelberg, DE (Pubs), p. 185.
Jefferis et al., (1990), "Molecular Definition of Interaction Sites on Human IgG for Fc Receptors huFcγR," Mol. Immunol., 27(12):1237-40.

Jones et al., (1986), "Replacing the Complementarity-Determining Regions in a Human Antibody with Those from a Mouse," Nature, 321:522-5.
Jung et al., (1986), "Activation of Human Peripheral Blood Mononuclear Cells by Anti-T3: Killing of Tumor Target Cells Coated with Anti-Target-Anti-T3 Conjugates," Proc Natl Acad Sci USA, 83:4479-83.
Junghans et al., (1996), "The Protection Receptor of IgG Catabolism is the B2-Microglobulin-Containing Neonatal Intestinal Transport Receptor," Proc Natl Acad Sci USA, 93(11):5512-6.
Kappel et al., (1992), "Regulating Gene Expression in Transgenic Animals," Curr Opin Biotech, 3:548-53.
Karpovsky et al., (1984), "Production of Target-Specific Effector Cells using Hetero-Cross Linked Aggregate Containing Anti-Target Cell and AntiFcγ Receptor Antibodies," J Exp Med, 1609(6):1686-701.
Kendra et al., (1999), "Pharmacokinetics and Stability of the ch14.18-Interleukin-2 Fusion Protein in Mice," Cancer Immunol Immunother, 48:219-29.
Kim et al., (1999), "Cytokine Molecular Adjuvants Modulate Immune Responses Induced by DNA Vaccine Constructs for HIV-1 and SIV," J Interfer Cytok Res, 19:77-84.
Kranz et al., (1984), "Attachment of an Anti-Receptor Antibody to Non-Target Cells Renders Them Susceptible to Lysis by a Clone of Cytotoxic T Lymphocytes," Proc Natl Acad Sci USA, 81:7922-6.
Kushner et al., (2001), "Phase II Trial of the Anti-GD2 Monoclonal Antibody 3F8 and Granulocyte-Macrophage Colony-Stimulating Factor for Neuroblastoma," J Clin Onco, 19(22):4189-94.
Lanza et al., (1993), "Active Immunity against the CD4 Receptor by Using an Antibody Antigenized with Residues 41-55 of the First Extracellular Domain," Proc Natl Acad Sci USA, 90:11683-7.
Lazar et al., (1988), "Transforming Growth Factor α: Mutation of Aspartic Acid 47 and Leucine 48 Results in Different Biological Activities," Mol Cell Biol, 8(3):1247-52.
Liu et al., (1985), "Heteroantibody Duplexes Target Cells for Lysis by Cytotoxic T Lymphocytes," Proc Natl Acad Sci USA, 82:8648-52.
Lo et al., (1992), "Expression and Secretion of an Assembled Tetrameric CH2-Deleted Antibody in *E. coli*.," Hum Antibod Hybridomas, 3:123-8.
Lo et al., (1998), "High Level Expression and Secretion of Fc-X Fusion Proteins in Mammalian Cells," Prot Engin, 11(6):495-500.
MacLean et al., (1996), "Enhancing the Effect of Theratope STn-KLH Cancer Vaccine in Patients with Metastatic Breast Cancer by Pretreatment with Low-Dose Intravenous Cyclophosphamide," J Immunother, 19(4):309-16.
Maloney et al., (1994), "Phase I Clinical Trial Using Escalating Single-Dose Infusion of Chimeric Anti-CD20 Monoclonal Antibody (IDEC-C2B8) in Patients with Recurrent B-Cell Lymphoma," Blood, 84(8):2457-66.
Manjula et al. (1976) "Subunit Interactions in Mouse Myeloma Proteins with Anti-Galactan Activity," Proc Natl Acad Sci, 73(3):932-6.
Mariani et al., (1997), "Tumor Targeting Potential of the Monoclonal Antibody BC-1 against Oncofetal Fibronectin in Nude Mice Bearing Human Tumor Implants," Cancer, 80:2378-4.
Martin et al., (2001), "Crystal Structure at 2.8 .ANG. of an FcRn/Heterodimeric Fc Complex: Mechanism of pH-Dependent Binding," Mol Cell., 7(4):867-77.
Mateo et al., (2000), "Removal of Amphipathic Epitopes from Genetically Engineered Antibodies: Production of Modified Immunoglobulins with Reduced Immunogenicity," Hybridoma, 19(6):463-71.
McMahan et al., (1991), "A Novel IL-1 Receptor, Cloned From B-Cells by Mammalian Expression is Expressed in Many Cell Types," EMBO J., 10:2821-32.
Medesan et al., (1997), "Delineation of the Amino Acid Residues Involved in Transcytosis and Catabolism of Mouse IgG1," Immunology, 158(5):2211-7.
Menard et al., (1983), "Generation of Monoclonal Antibodies Reacting with Normal and Cancer Cells of Human Breast," Cancer Res, 43:1295-300.

(56) References Cited

OTHER PUBLICATIONS

Metelitsa et al., (2002), "Antidisialoganglioside/Granulocyte Macrophage-Colony-Stimulating Factor Fusion Protein Facilitates Neutrophil Antibody-Dependent Cellular Cytotoxicity and Depends on Fc.γ.RII (CD32) and Mac-1 (CD11b/CD18) for Enhanced Effector Cell Adhesion and Azurophil Granule Exocytosis," Blood, 99(11):4166-73.
Miyake et al., (1988), "Synthesis of Recombinant Human Single-Chain Urokinase-Type Plasminogen Activator Variants Resistant to Plasmin and Thrombin," Biochemistry, 104:643-7.
Morrison et al., (1984), "Chimeric Human Antibody Molecules: Mouse Antigen-Binding Domains with Human Constant Region Domains," Proc Natl Acad Sci USA, 81:6851-5.
Mueller et al., (1990), "Enhancement of Antibody-Dependent Cytotoxicity with a Chimeric Anti-GD2 Antibody," Immunology, 144(4):1382-6.
Mueller et al., (1990), "Serum Half-Life and Tumor Localization of a Chimeric Antibody Deleted of the CH2 Domain and Directed Against the Disialoganglioside GD2," Proc Natl Acad Sci USA., 87:5702-5.
Mueller et al., (1997), "Humanized Porcine VCAM-Specific Monoclonal Antibodies with Chimeric IgG2/G4 Constant Regions Block Human Leukocyte Binding to Procine Endothelial Cells," Mol Immunol, 34(6):441-52.
Mujoo et al., (1987), "Disialoganglioside GD2 on Human Neuroblastoma Cells: Target Antigen for Monoclonal Antibody-Mediated Cytolysis and Suppression of Tumor Growth," Cancer Res. 47(4):1098-1104.
Murphy et al., (1986), "Genetic Construction, Expression, and Melanoma-Selective Cytotoxicity of a Diphtheria Toxin-Related .alpha.-Melanocyte-Stimulating Hormone Fusion Protein," Proc Natl Acad Sci USA, 83:8258-62.
Murphy, "Diphtheria-Related Peptide Hormone Gene Fusions: A Molecular Gene Approach to Chimeric Toxin Development," *Immunotoxins*,, (1st Ed, 1988), vol. 37 in the series *Cancer Treatment and Research*, S T Rosen (Ed), Springer US, New York, NY (Pub) pp. 123-140.
Naramura et al., (1993), "Therapeutic Potential of Chimeric and Murine Anti-(Epidermal Growth Factor Receptor) Antibodies in a Metastasis Model for Human Melanoma," Cancer Immuno Immunother, 37:343-9.
Nastala et al., (1994), "Recombinant IL-12 Administration Induces Tumor Regression in Association with IFNα Production," Immunol., 153:1697-706.
Neal et al., (2003), "NXS2 Murine Neuroblastomas Express Increased Levels of MHC Class I Antigens upon Recurrence Following NK-Dependent Immunotherapy," Cancer Immunol Immunother, 53:41-52.
Neal et al., (2004), "Enhanced Activity of Hu14.18-IL2 Immunocytokine against Murine NXS2 Neuroblastoma when Combined with Interleukin-2 Therapy," Clin Cancer. Res, 10:4839-47.
Nedwin et al., (1985), "Human Lymphotoxin and Tumor Necrosis Factor Genes: Structure, Homology and Chromosomal Localization," Nucl Acids Res, 13(17):6361-73.
Nelles et al., (1987), "Characterization of Recombinant Human Single Chain Urokinase-Type Plaminogen Activtor Mutants Produced by Site-Specific Mutagenesis of Lysine 158," Biol Chem, 262(12):5682-9.
Neuberger et al., (1984), "Recombinant Antibodies Possessing Novel Effector Functions," Nature, 312:604-8.
Ngo et al., (1994), "Computational Complexity, Protein Structure Prediction, and the Levinthal Paradox," *The Protein Folding Problem and Tertiary Structure Prediction*, (1$^{st}$ Ed, 1994), K M Merz and S M Le Grand (Eds.), Birkhäuser, Boston, MA (Pub), pp. 433-440 and 492-495.
Orlandi et al., (1989), "Cloning Immunoglobulin Variable Domains for Expression by the Polymerase Chain Reaction," Proc Natl Acad Sci USA, 86:3833-7.
Pastan et al., (1989), "Pseudomonas Exotoxin: Chimeric Toxins," Biol Chem, 264(26):15157-60.

Paul et al., (1988), "Lymphotoxin," Ann Rev Immunol, 6:407-38.
Perez et al., (1989), "Isolation and Characterization of a cDNA Encoding the KS1/4 Epithelial Carcinoma Marker," Immunology, 142(10):3662-7.
Poon et al., (1995), "Structure and Function of Several Anti-Dansyl Chimeric Antibodies Formed by Domain Interchanges Between Human IgM and Mouse IgG2b," Biol Chem, 270:8571-7.
Queen et al., (1989), "A Humanized Antibody that Binds to the Interleukin 2 Receptor," Proc Natl Acad Sci USA, 86:10029-33.
Reisfeld et al., (1994), "Potential of Genetically Engineered Anti-Ganglioside GD2 Antibodies for Cancer Immunotherapy," Prog Brain Res, 101:201-12.
Riechmann et al., (1988), "Reshaping Human Antibodies for Therapy," Nature, 332:323-7.
Riethmuller et al., (1994), "Randomised Trial of Monoclonal Antibody for Adjuvant Therapy of Resected Dukes' C Colorectal Carcinoma," The Lancet, 343:1177-83.
Robinson et al., (1998), "Optimizing the Stability of Single-Chain Proteins by Linker Length and Composition Mutagenesis," Proc Natl Acad Sci USA, 95:5929-34.
Rudikoff et al., (1982), "Single Amino Acid Substitution Altering Antigen-Binding Specificity," Proc Natl Acad Sci USA, 79(6):1978-3.
Sakano et al., (1980), "Two Types of Somatic Recombination are Necessary for the Generation of Complete Immunoglobin Heavy-Chain Genes," Nature, 286:676-83.
Saleh et al., (1992), "Phase I Trial of the Chimeric Anti-GD2 Monoclonal Antibody ch14.18 in Patients With Malignant Melanoma," Hum Antiob Hybridomas, 3:19-24.
Santon et al., (1986), "Effects of Epidermal Growth Factor Receptor Concentration on Tumorigenicity of A431 Cells in Nude Mice," Cancer Res, 46:4701-5.
Schlom, "Monoclonal Antibodies: They're More and Less Than You Think," *Molecular Foundations of Oncology*, (1$^{st}$ Ed, 1991), S Broder (Ed), Lippincott, Williams & Wilkins, Philadelphia, Pa (Pub), pp. 95-133.
Schwartzberg et al., (2001), "Clinical Experience with Edrecolomab: A Monoclonal Antibody Therapy for Colon Carcinoma," Crit Rev Oncol Hematol, 40:17-24.
Senior et al., (2000), "Cleavage of a Recombinant Human Immunoglobulin A2 (igA2)-IgA1 Hybrid Antibody by Certain Bacterial IgA1 Proteases," Infect Immun, 68(2):463-9.
Sharma et al., (1999), "T Cell-Derived IL-10 Promotes Lung Cancer Growth by Suppressing Both T Cell and APC Function," Immunology, 163:5020-8.
Sharp et al., (1988), "Codon Usage Patterns in *Escherichia coli, Bacillus subtilis, Saccharomyces cerevisiae, Schizosaccharomyces pombe, Drosophila melanogaster* and *Homo sapiens*; A Review of the Considerable Within-Species Diversity," Nucl Acids Res, 16(17):8207-11.
Shen et al., (1986), "Heteroantibody-Mediated Cytotoxicity: Antibody to the High Affinity Fc Receptor for IgG Mediates Cytotoxicity by Human Monocytes that is Enhanced by Interferon-γ. and is Not Blocked by Human IgG," Immunology, 137(11):3378-82.
Shinkawa et al., (2003), "The Absence of Fucose but not the Presence of Galactose or Bisecting N-Acetylglucosamine of Human IgG1 Complex-Type Oligosaccharides Shows the Critical Role of Enhancing Antibody-Dependent Cellular Cytotoxicity," Biol Chem, 278(5): 3466-73.
Skolnick and Fetrow, (2000), "From Genes to Protein Structure and Function: Novel Applications of Computational Approaches in the Genomic Era," Trends Biotech, 18(1):34-9.
Spiekermann et al., (2002), "Receptor-Mediated Immunoglobulin G Transport Across Mucosal Barriers in Adult Life: Functional Expression of FcRn in the Mammalian Lung," Exp Med, 196:303-10.
Stevenson et al., (1997), "Conjugation of Human Fcγ in Closed-Hinge or Open-Hinge Configuration to Fab'γ and Analogous Ligands," Immunology, 158:2242-50.
Takai, (2002), "Roles of Fc Receptors in Autoimmunity," Nat Rev Immunol, 2(8):580-92.

(56) References Cited

OTHER PUBLICATIONS

Tao et al., (1989), "Studies of Aglycosylated Chimeric Mouse IgG: Role of Carbohydrate in the Structure and Effector Functions Mediated by the Human IgG Constant Region," Immunology, 143(8):2595-601.

Tao et al., (1993), "Structural Features of Human Immunoglobulin G that Determine Isotype-Differences in Complement Activation," J Exp Med, 178(2):661-7.

*The Merck Manual of Diagnosis and Therapy*, (17th Ed, 1999), R S Porter and M H Beers (Eds), Merck Sharp & Dohme Corp., Kenilworth, NH (Pub), pp. 990-993 and 1278-1283.

Thommesen et al., (2000), "Lysine 322 in the Human IgG3 CH2 Domain is Crucial for Antibody Dependent Complement Activation," Mol Immunol, 37(16):995-1004.

Tiruppathi et al., (1996), "Isolation and Characterization of a Cell Surface Albumin-Binding Protein from Vascular Endothelial Cells," Proc Nat Acad Sci USA, 93:250-4.

Vagliani et al., (1996), "Interleukin 12 Potentiates the Curative Effect of a Vaccine Based on Interleukin 2-Transduced Tumor Cells," Cancer Res, 56:467-70.

Varki et al., (1984), "Antigens Associated with a Human Lung Adenocarcinoma Defined by Monoclonal Antibodies," Cancer Res, 44:681-7.

Voest et al., (1995), "Inhibition of Angiogenesis in Vivo by Interleukin 12," J Natl Cancer Inst, 87:581-6.

Ward et al., (1995), "The Effector Functions of Immunoglobulins: Implications for Therapy," Ther Immunol, 2:77-94.

Weber et al., (2001), "Phase I Trial of huKS-IL2 Immunocytokine in Patients with Prostate Carcinoma: Clinical, PK, and Biological PD Results," Am Sec Clin Oncol Proc, 20(Part 1):259a (Abstract).

Weitkamp et al., (1973), "Additional Data on the Population Distribution of Human Serum Albumin Genes; Three New Variants," Ann Hum Genet, 37:219-26.

Wells, (1990), "Additivity of Mutational Effect in Proteins," Biochemistry, 29(37):8509-17.

Went et al., (2004), "Frequent EpCam Protein Expression in Human Carcinomas," Hum Pathol, 35(1):122-8.

Woof et al., (1986), "Localisation of the Monocyte-Binding Region on Human Immunoglobulin G," Mol Immunol, 23:319-30.

Written Opinion of the International Searching Authority for International Application No. PCT/EP2005/000428, dated Oct. 10, 2005 (6 pages).

Wysocka et al., (1995), "Interleukin-12 is Required for Interferon-γ Production and Lethality in Lipopolysaccharide-Induced Shock in Mice," Eur J Immunol, 25:672-6.

Xu et al., (1994), "Residue at Position 331 in the IgG1 and IgG4 CH2 Domains Contributes to Their Differential Ability to Bind and Activate Complement," J Biol Chem, 269(5):3469-74.

Yan et al., (1996), "Characterization of an Ig VH Idiotope that Results in Specific Homophilic Binding and Increased Avidity for Antigen," Immunology, 157:1582-8.

Yeh et al., (1992), "Design of Yeast-Secreted Albumin Derivatives for Human Therapy: Biological and Antiviral Properties of a Serum Albumin-CD4 Genetic Conjugate," Proc Natl Acad Sci USA, 89:1904-8.

Yu et al., (1998), "Phase I Trial of a Human-Mouse Chimeric Anti-Disialoganglioside Monoclonal Antibody ch14.18 in Patients with Refractory Neuroblastoma and Osteosarcoma," J Clin Oncol, 16(6):2169-80.

Zeng et al., (2005), "Anti-Neuroblastoma Effect of ch14.18 Antibody Produced in CHO Cells is Mediated by NK-cells in Mice," Mol Immunol, 42(11):1311-9.

Zhu et al., (2001), "MHC Class I-Related Neonatal Fc Receptor for IgG is Functionally Expressed in Monocytes, Intestinal Macrophages and Dendritic Cells," Immunology, 166:3266-76.

Zuckier et al., (1998), "Chimeric Human-Mouse IgG Antibodies with Shuffled Constant Region Exons Demonstrate that Multiple Domains Contribute to in vivo Half-Life," Cancer Res, 58(17):3905-8.

U.S. Appl. No. 11/040,071, filed Jan. 21, 2005, Anti-Cancer Antibodies With Reduced Complement Fixation.

U.S. Appl. No. 12/209,935, filed Sep. 12, 2008, Anti-Cancer Antibodies With Reduced Complement Fixation.

U.S. Appl. No. 14/478,753, filed Sep. 5, 2014, Anti-Cancer Antibodies With Reduced Complement Fixation.

\* cited by examiner

Hu14.18 IgG1 Mature Heavy Chain

EVQLVQSGAEVEKPGASVKISCKASGSSFTGYNMNWVRQNIGKSLEWIGAIDPYYGGTSYNQKF
KGRATLTVDKSTSTAYMHLKSLRSEDTAVYYCVSGMEYWGQGTSVTVSSASTKGPSVFPLAPSS
KSTSGGTAALGCLVKDYFPEPVTVSWNSGALTSGVHTFPAVLQSSGLYSLSSVVTVPSSSLGTQ
TYICNVNHKPSNTKVDKRVEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYKCAVS
NKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK
(SEQ ID NO: 1)

FIG. 1

Hu14.18 IgG1 Mature Heavy Chain with K322A Mutation

EVQLVQSGAEVEKPGASVKISCKASGSSFTGYNMNWVRQNIGKSLEWIGAIDPYYGGTSYNQKF
KGRATLTVDKSTSTAYMHLKSLRSEDTAVYYCVSGMEYWGQGTSVTVSSASTKGPSVFPLAPSS
KSTSGGTAALGCLVKDYFPEPVTVSWNSGALTSGVHTFPAVLQSSGLYSLSSVVTVPSSSLGTQ
TYICNVNHKPSNTKVDKRVEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYKCAVS
NAALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGK
(SEQ ID NO: 5)

FIG. 2

Hu14.18 IgG1 Mature Light Chain

DVVMTQTPLSLPVTPGEPASISCRSSQSLVHRNGNTYLHWYLQKPGQSPKLLIHKVSNRFSGVP
DRFSGSGSGTDFTLKISRVEAEDLGVYFCSQSTHVPPLTFGAGTKLELKRTVAAPSVFIFPPSD
EQLKSGTASVVCLLNNFYPREAKVQWKVDNALQSGNSQESVTEQDSKDSTYSLSSTLTLSKADY
EKHKVYACEVTHQGLSSPVTKSFNRGEC(SEQ ID NO: 2)

FIG. 3

Hu14.18 IgG1 Mature Heavy chain Coding Sequence, with Introns:

```
GAGGTGCAGCTGGTGCAGTCCGGCGCCGAGGTGGAGAAGCCCGGCGCCTCCGTGAAGATCTCCT
GCAAGGCCTCCGGCTCCTCCTTCACCGGCTACAACATGAACTGGGTGCGCCAGAACATCGGCAA
GTCCCTGGAGTGGATCGGCGCCATCGACCCCTACTACGGCGGCACCTCCTACAACCAGAAGTTC
AAGGGCCGCGCCACCCTGACCGTGGACAAGTCCACCTCCACCGCCTACATGCACCTGAAGTCCC
TGCGCTCCGAGGACACCGCCGTGTACTACTGCGTGTCCGGCATGGAGTACTGGGGCCAGGGCAC
CTCCGTGACCGTGTCCTCCGGTAAGCTTTTCTGGGGCAGGCCAGGCCTGACCTTGGCTTTGGGG
CAGGGAGGGGGCTAAGGTGAGGCAGGTGGCGCCAGCCAGGTGCACACCCAATGCCCATGAGCCC
AGACACTGGACGCTGAACCTCGCGGACAGTTAAGAACCCAGGGGCCTCTGCGCCCTGGGCCCAG
CTCTGTCCCACACCGCGGTCACATGGCACCACCTCTCTTGCAGCCTCCACCAAGGGCCCATCGG
TCTTCCCCCTGGCACCCTCCTCCAAGAGCACCTCTGGGGGCACAGCGGCCCTGGGCTGCCTGGT
CAAGGACTACTTCCCCGAACCGGTGACGGTGTCGTGGAACTCAGGCGCCCTGACCAGCGGCGTG
CACACCTTCCCGGCTGTCCTACAGTCCTCAGGACTCTACTCCCTCAGCAGCGTGGTGACCGTGC
CCTCCAGCAGCTTGGGCACCCAGACCTACATCTGCAACGTGAATCACAAGCCCAGCAACACCAA
GGTGGACAAGAGAGTTGGTGAGAGGCCAGCACAGGGAGGGAGGGTGTCTGCTGGAAGCCAGGCT
CAGCGCTCCTGCCTGGACGCATCCCGGCTATGCAGTCCCAGTCCAGGGCAGCAAGGCAGGCCCC
GTCTGCCTCTTCACCCGGAGGCCTCTGCCCGCCCCACTCATGCTCAGGGAGAGGGTCTTCTGGC
TTTTTCCCCAGGCTCTGGGCAGGCACAGGCTAGGTGCCCCTAACCCAGGCCCTGCACACAAAGG
GGCAGGTGCTGGGCTCAGACCTGCCAAGAGCCATATCCGGGAGGACCCTGCCCCTGACCTAAGC
CCACCCCAAAGGCCAAACTCTCCACTCCCTCAGCTCGGACACCTTCTCTCCTCCCAGATTCCAG
TAACTCCCAATCTTCTCTCTGCAGAGCCCAAATCTTGTGACAAAACTCACACATGCCCACCGTG
CCCAGGTAAGCCAGCCCAGGCCTCGCCCTCCAGCTCAAGGCGGGACAGGTGCCCTAGAGTAGCC
TGCATCCAGGGACAGGCCCCAGCCGGGTGCTGACACGTCCACCTCCATCTCTTCCTCAGCACCT
GAACTCCTGGGGGGACCGTCAGTCTTCCTCTTCCCCCCAAAACCCAAGGACACCCTCATGATCT
CCCGGACCCCTGAGGTCACATGCGTGGTGGTGGACGTGAGCCACGAAGACCCTGAGGTCAAGTT
CAACTGGTACGTGGACGGCGTGGAGGTGCATAATGCCAAGACAAAGCCGCGGGAGGAGCAGTAC
AACAGCACGTACCGTGTGGTCAGCGTCCTCACCGTCCTGCACCAGGACTGGCTGAATGGCAAGG
AGTACAAGTGCGCTGTCTCCAACAAAGCCCTCCCAGCCCCCATCGAGAAAACCATCTCCAAAGC
CAAAGGTGGGACCCGTGGGGTGCGAGGGCCACATGGACAGAGGCCGGCTCGGCCCACCCTCTGC
CCTGAGAGTGACCGCTGTACCAACCTCTGTCCCTACAGGGCAGCCCCGAGAACCACAGGTGTAC
ACCCTGCCCCCATCACGGGAGGAGATGACCAAGAACCAGGTCAGCCTGACCTGCCTGGTCAAAG
GCTTCTATCCCAGCGACATCGCCGTGGAGTGGGAGAGCAATGGGCAGCCGGAGAACAACTACAA
GACCACGCCTCCCGTGCTGGACTCCGACGGCTCCTTCTTCCTCTATAGCAAGCTCACCGTGGAC
AAGAGCAGGTGGCAGCAGGGGAACGTCTTCTCATGCTCCGTGATGCATGAGGCTCTGCACAACC
ACTACACGCAGAAGAGCCTCTCCCTGTCCCGGGTAAA(SEQ ID NO: 3)
```

FIG. 4

Hu14.18 IgG1 Mature Light chain Coding Sequence, with Introns:

GACGTGGTGATGACCCAGACCCCCCTGTCCCTGCCCGTGACCCCCGGCGAGCCCGCCTCCATCT
CCTGCAGATCTAGTCAGAGTCTTGTACACCGTAATGGAAACACCTATTTACATTGGTACCTGCA
GAAGCCAGGCCAGTCTCCAAAGCTCCTGATTCACAAAGTTTCCAACCGATTTTCTGGGGTCCCA
GACAGGTTCAGTGGCAGTGGATCAGGGACAGATTTCACACTCAAGATCAGCAGAGTGGAGGCTG
AGGATCTGGGAGTTTATTTCTGTTCTCAAAGTACACATGTTCCTCCGCTCACGTTCGGTGCTGG
GACCAAGCTGGAGCTGAAACGTATTAGTGTGTCAGGGTTTCACAAGAGGGACTAAAGACATGTC
AGCTATGTGTGACTAATGGTAATGTCACTAAGCTGCGGGATCCCGCAATTCTAAACTCTGAGGG
GGTCGGATGACGTGGCCATTCTTTGCCTAAAGCATTGAGTTTACTGCAAGGTCAGAAAAGCATG
CAAAGCCCTCAGAATGGCTGCAAAGAGCTCCAACAAAACAATTTAGAACTTTATTAAGGAATAG
GGGGAAGCTAGGAAGAAACTCAAAACATCAAGATTTTAAATACGCTTCTTGGTCTCCTTGCTAT
AATTATCTGGGATAAGCATGCTGTTTTCTGTCTGTCCCTAACATGCCCTGTGATTATCCGCAAA
CAACACACCCAAGGGCAGAACTTTGTTACTTAAACACCATCCTGTTTGCTTCTTTCCTCAGGAA
CTGTGGCTGCACCATCTGTCTTCATCTTCCCGCCATCTGATGAGCAGTTGAAATCTGGAACTGC
CTCTGTTGTGTGCCTGCTGAATAACTTCTATCCCAGAGAGGCCAAAGTACAGTGGAAGGTGGAT
AACGCCCTCCAATCGGGTAACTCCCAGGAGAGTGTCACAGAGCAGGACAGCAAGGACAGCACCT
ACAGCCTCAGCAGCACCCTGACGCTGAGCAAAGCAGACTACGAGAAACACAAAGTCTACGCCTG
CGAAGTCACCCATCAGGGCCTGAGCTCGCCCGTCACAAAGAGCTTCAACAGGGGAGAGTGT
(SEQ ID NO: 4)

FIG. 5

Amino Acid Sequence of the Mature Fusion Protein Human 14.18 sFv (VL-VH)-Fc

DVVMTQTPLSLPVTPGEPASISCRSSQSLVHRNGNTYLHWYLQKPGQSPKLLIHKVSNRFSGVP
DRFSGSGSGTDFTLKISRVEAEDLGVYFCSQSTHVPPLTFGAGTKLELKSGGGGSGGGGSGGGG
SGGGGSEVQLVQSGAEVEKPGASVKISCKASGSSFTGYNMNWVRQNIGKSLEWIGAIDPYYGGT
SYNQKFKGRATLTVDKSTSTAYMHLKSLRSEDTAVYYCVSGMEYWGQGTSVTVSSEPKSCDKTH
TCPPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLP
PSREEMTKNQVSLTCLVKGFYPSDIAVEWESNGQPENNYKTTPPVLDSDGSFFLYSKLTVDKSR
WQQGNVFSCSVMHEALHNHYTQKSLSLSPGK(SEQ ID NO:9)

FIG. 11

DNA Sequence encoding the mature fusion protein Human 14.18 sFv (VL-VH)-Fc, with introns:

GACGTGGTGATGACCCAGACCCCCCTGTCCCTGCCCGTGACCCCCGGCGAGCCCGCCTCCATCT
CCTGCAGATCTAGTCAGAGTCTTGTACACCGTAATGGAAACACCTATTTACATTGGTACCTGCA
GAAGCCAGGCCAGTCTCCAAAGCTCCTGATTCACAAAGTTTCCAACCGATTTTCTGGGGTCCCA
GACAGGTTCAGTGGCAGTGGATCAGGGACAGATTTCACACTCAAGATCAGCAGAGTGGAGGCTG
AGGATCTGGGAGTTTATTTCTGTTCTCAAAGTACACATGTTCCTCCGCTCACGTTCGGTGCTGG
GACCAAGCTGGAGCTGAAATCCGGAGGCGGTGGGTCGGGAGGTGGCGGGTCTGGTGGTGGAGGC
AGCGGTGGTGGGGGATCCGAGGTGCAGCTGGTGCAGTCCGGCGCCGAGGTGGAGAAGCCCGGCG
CCTCCGTGAAGATCTCCTGCAAGGCCTCCGGCTCCTCCTTCACCGGCTACAACATGAACTGGGT
GCGCCAGAACATCGGCAAGTCCCTGGAGTGGATCGGCGCCATCGACCCCTACTACGGCGGCACC
TCCTACAACCAGAAGTTCAAGGGCCGCGCCACCCTGACCGTGGACAAGTCCACCTCCACCGCCT
ACATGCACCTGAAGTCCCTGCGCTCCGAGGACACCGCCGTGTACTACTGCGTGTCCGGCATGGA
GTACTGGGGCCAGGGCACCTCCGTGACCGTGTCCTCCGAGCCCAAATCTTGTGACAAAACTCAC
ACATGCCCACCGTGCCCAGGTAAGCCAGCCCAGGCCTCGCCCTCCAGCTCAAGGCGGGACAGGT
GCCCTAGAGTAGCCTGCATCCAGGGACAGGCCCCAGCCGGGTGCTGACACGTCCACCTCCATCT
CTTCCTCAGCACCTGAACTCCTGGGGGGACCGTCAGTCTTCCTCTTCCCCCCAAAACCCAAGGA
CACCCTCATGATCTCCCGGACCCCTGAGGTCACATGCGTGGTGGTGGACGTGAGCCACGAAGAC
CCTGAGGTCAAGTTCAACTGGTACGTGGACGGCGTGGAGGTGCATAATGCCAAGACAAAGCCGC
GGGAGGAGCAGTACAACAGCACGTACCGTGTGGTCAGCGTCCTCACCGTCCTGCACCAGGACTG
GCTGAATGGCAAGGAGTACAAGTGCAAGGTCTCCAACAAAGCCCTCCCAGCCCCCATCGAGAAA
ACCATCTCCAAAGCCAAAGGTGGGACCCGTGGGGTGCGAGGGCCACATGGACAGAGGCCGGCTC
GGCCCACCCTCTGCCCTGAGAGTGACCGCTGTACCAACCTCTGTCCCTACAGGGCAGCCCCGAG
AACCACAGGTGTACACCCTGCCCCCATCCCGGGAGGAGATGACCAAGAACCAGGTCAGCCTGAC
CTGCCTGGTCAAAGGCTTCTATCCCAGCGACATCGCCGTGGAGTGGGAGAGCAATGGGCAGCCG
GAGAACAACTACAAGACCACGCCTCCCGTGCTGGACTCCGACGGCTCCTTCTTCCTCTATAGCA
AGCTCACCGTGGACAAGAGCAGGTGGCAGCAGGGGAACGTCTTCTCATGCTCCGTGATGCATGA
GGCTCTGCACAACCACTACACGCAGAAGAGCCTCTCCCTGTCCCGGGTAAATGA(SEQ ID NO:8)

FIG. 12

SEQUENCE LISTING

<160> NUMBER OF SEQ ID NOS: 10

<210> SEQ ID NO 1
<211> LENGTH: 443
<212> TYPE: PRT
<213> ORGANISM: Homo sapiens

<400> SEQUENCE: 1

```
Glu Val Gln Leu Val Gln Ser Gly Ala Glu Val Glu Lys Pro Gly Ala
1               5                   10                  15

Ser Val Lys Ile Ser Cys Lys Ala Ser Gly Ser Phe Thr Gly Tyr
            20                  25                  30

Asn Met Asn Trp Val Arg Gln Asn Ile Gly Lys Ser Leu Glu Trp Ile
            35                  40                  45

Gly Ala Ile Asp Pro Tyr Tyr Gly Gly Thr Ser Tyr Asn Gln Lys Phe
        50                  55                  60

Lys Gly Arg Ala Thr Leu Thr Val Asp Lys Ser Thr Ser Thr Ala Tyr
65                  70                  75                  80

Met His Leu Lys Ser Leu Arg Ser Glu Asp Thr Ala Val Tyr Tyr Cys
                85                  90                  95

Val Ser Gly Met Glu Tyr Trp Gly Gln Gly Thr Ser Val Thr Val Ser
                100                 105                 110

Ser Ala Ser Thr Lys Gly Pro Ser Val Phe Pro Leu Ala Pro Ser Ser
                115                 120                 125

Lys Ser Thr Ser Gly Gly Thr Ala Ala Leu Gly Cys Leu Val Lys Asp
            130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
                180                 185                 190

Thr Tyr Ile Cys Asn Val Asn His Lys Pro Ser Asn Thr Lys Val Asp
            195                 200                 205

Lys Arg Val Glu Pro Lys Ser Cys Asp Lys Thr His Thr Cys Pro Pro
210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
                260                 265                 270

Trp Tyr Val Asp Gly Val Glu Val His Asn Ala Lys Thr Lys Pro Arg
            275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Ala Val Ser
305                 310                 315                 320
```

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 2
<211> LENGTH: 220
<212> TYPE: PRT
<213> ORGANISM: Homo sapiens

<400> SEQUENCE: 2

Asp Val Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Arg
            20                  25                  30

Asn Gly Asn Thr Tyr Leu His Trp Tyr Leu Gln Lys Pro Gly Gln Ser
        35                  40                  45

Pro Lys Leu Leu Ile His Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Leu Thr Phe Gly Ala Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 3
<211> LENGTH: 2150
<212> TYPE: DNA
<213> ORGANISM: Homo sapiens

<400> SEQUENCE: 3

```
gaggtgcagc tggtgcagtc cggcgccgag gtggagaagc ccggcgcctc cgtgaagatc    60
tcctgcaagg cctccggctc ctccttcacc ggctacaaca tgaactgggt gcgccagaac   120
atcggcaagt ccctggagtg gatcggcgcc atcgacccct actacggcgg cacctcctac   180
aaccagaagt tcaagggccg cgccaccctg accgtggaca gtccacctc caccgcctac    240
atgcacctga gtccctgcg ctccgaggac accgccgtgt actactgcgt gtccggcatg   300
gagtactggg gccagggcac ctccgtgacc gtgtcctccg gtaagctttt ctggggcagg   360
ccaggcctga ccttggcttt ggggcaggga gggggctaag gtgaggcagg tggcgccagc   420
caggtgcaca cccaatgccc atgagcccag acactggacg ctgaacctcg cggacagtta   480
agaacccagg ggcctctgcg ccctgggccc agctctgtcc cacaccgcgg tcacatggca   540
ccacctctct tgcagcctcc accaagggcc catcggtctt ccccctggca ccctcctcca   600
agagcacctc tgggggcaca gcggccctgg gctgcctggt caaggactac ttccccgaac   660
cggtgacggt gtcgtggaac tcaggcgccc tgaccagcgg cgtgcacacc ttcccggctg   720
tcctacagtc ctcaggactc tactccctca gcagcgtggt gaccgtgccc tccagcagct   780
tgggcaccca gacctacatc tgcaacgtga atcacaagcc cagcaacacc aaggtggaca   840
agagagttgg tgagaggcca gcacaggag ggagggtgtc tgctggaagc caggctcagc    900
gctcctgcct ggacgcatcc cggctatgca gtcccagtcc agggcagcaa ggcaggcccc   960
gtctgcctct tcacccggag gcctctgccc gccccactca tgctcaggga gagggtcttc  1020
tggcttttc cccaggctct gggcaggcac aggctaggtg ccctaaccc aggccctgca   1080
cacaaagggg caggtgctgg gctcagacct gccaagagcc atatccggga ggaccctgcc  1140
cctgacctaa gcccacccca aaggccaaac tctccactcc ctcagctcgg acaccttctc  1200
tcctcccaga ttccagtaac tcccaatctt ctctctgcag agcccaaatc ttgtgacaaa  1260
actcacacat gcccaccgtg cccaggtaag ccagcccagg cctcgccctc cagctcaagg  1320
cgggacaggt gccctagagt agcctgcatc cagggacagg ccccagccgg gtgctgacac  1380
gtccacctcc atctcttcct cagcacctga actcctgggg ggaccgtcag tcttcctctt  1440
cccccccaaaa cccaaggaca ccctcatgat ctcccggacc cctgaggtca catgcgtggt  1500
ggtggacgtg agccacgaag accctgaggt caagttcaac tggtacgtgg acggcgtgga  1560
ggtgcataat gccaagacaa agccgcggga ggagcagtac aacagcacgt accgtgtggt  1620
cagcgtcctc accgtcctgc accaggactg gctgaatggc aaggagtaca agtgcgctgt  1680
ctccaacaaa gccctcccag cccccatcga gaaaaccatc tccaaagcca aggtgggac   1740
ccgtggggtg cgagggccac atggacagag gccggctcgg cccacctct gcctgagag     1800
tgaccgctgt accaacctct gtccctacag ggcagccccg agaaccacag gtgtacaccc   1860
tgccccccatc acgggaggag atgaccaaga ccaggtcag cctgacctgc ctggtcaaag   1920
gcttctatcc cagcgacatc gccgtggagt gggagagcaa tgggcagccg gagaacaact   1980
acaagaccac gcctcccgtg ctggactccg acggctcctt cttcctctat agcaagctca   2040
ccgtggacaa gagcaggtgg cagcagggga acgtcttctc atgctccgtg atgcatgagg   2100
ctctgcacaa ccactacacg cagaagagcc tctccctgtc cccgggtaaa             2150
```

<210> SEQ ID NO 4
<211> LENGTH: 1085
<212> TYPE: DNA

<213> ORGANISM: Homo sapiens

<400> SEQUENCE: 4

```
gacgtggtga tgacccagac cccctgtcc ctgcccgtga ccccggcga gcccgcctcc     60
atctcctgca gatctagtca gagtcttgta caccgtaatg gaaacaccta tttacattgg   120
tacctgcaga agccaggcca gtctccaaag ctcctgattc acaaagtttc caaccgattt   180
tctggggtcc cagacaggtt cagtggcagt ggatcaggga cagatttcac actcaagatc   240
agcagagtgg aggctgagga tctgggagtt tatttctgtt ctcaaagtac acatgttcct   300
ccgctcacgt tcggtgctgg gaccaagctg gagctgaaac gtattagtgt gtcagggttt   360
cacaagaggg actaaagaca tgtcagctat gtgtgactaa tggtaatgtc actaagctgc   420
gggatcccgc aattctaaac tctgagggg tcggatgacg tggccattct ttgcctaaag   480
cattgagttt actgcaaggt cagaaaagca tgcaaagccc tcagaatggc tgcaaagagc   540
tccaacaaaa caatttagaa ctttattaag aatagggg aagctaggaa gaaactcaaa   600
acatcaagat tttaaatacg cttccttggtc tccttgctat aattatctgg ataagcatg   660
ctgttttctg tctgtccta acatgccctg tgattatccg caaacaacac acccaagggc   720
agaactttgt tacttaaaca ccatcctgtt tgcttctttc ctcaggaact gtggctgcac   780
catctgtctt catcttcccg ccatctgatg agcagttgaa atctggaact gcctctgttg   840
tgtgcctgct gaataacttc tatcccagag aggccaaagt acagtggaag gtggataacg   900
ccctccaatc gggtaactcc caggagagtg tcacagagca ggacagcaag gacagcacct   960
acagcctcag cagcaccctg acgctgagca agcagacta cgagaaacac aaagtctacg   1020
cctgcgaagt cacccatcag ggcctgagct cgcccgtcac aaagagcttc aacaggggag   1080
agtgt                                                              1085
```

<210> SEQ ID NO 5
<211> LENGTH: 443
<212> TYPE: PRT
<213> ORGANISM: Artificial Sequence
<220> FEATURE:
<223> OTHER INFORMATION: Hu14.18 IgG1 Mature Heavy Chain with K322A Mutation

<400> SEQUENCE: 5

```
Glu Val Gln Leu Val Gln Ser Gly Ala Glu Val Glu Lys Pro Gly Ala
1               5                   10                  15

Ser Val Lys Ile Ser Cys Lys Ala Ser Gly Ser Ser Phe Thr Gly Tyr
            20                  25                  30

Asn Met Asn Trp Val Arg Gln Asn Ile Gly Lys Ser Leu Glu Trp Ile
        35                  40                  45

Gly Ala Ile Asp Pro Tyr Tyr Gly Gly Thr Ser Tyr Asn Gln Lys Phe
    50                  55                  60

Lys Gly Arg Ala Thr Leu Thr Val Asp Lys Ser Thr Ser Thr Ala Tyr
65                  70                  75                  80

Met His Leu Lys Ser Leu Arg Ser Glu Asp Thr Ala Val Tyr Tyr Cys
                85                  90                  95

Val Ser Gly Met Glu Tyr Trp Gly Gln Gly Thr Ser Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140
```

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Arg Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Ala Val Ser
305                 310                 315                 320

Asn Ala Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 6
<211> LENGTH: 21
<212> TYPE: DNA
<213> ORGANISM: Artificial sequence
<220> FEATURE:
<223> OTHER INFORMATION: Forward primer for pdHL7-hu14.18 plasmid DNA

<400> SEQUENCE: 6
tacaagtgcg ctgtctccaa c                                        21

<210> SEQ ID NO 7
<211> LENGTH: 22
<212> TYPE: DNA
<213> ORGANISM: Artificial Sequence
<220> FEATURE:
<223> OTHER INFORMATION: Reverse primer for pdHL7-hu14.18 plasmid DNA

<400> SEQUENCE: 7
tgttggagac agcgcacttg ta                                              22

<210> SEQ ID NO 8
<211> LENGTH: 1655
<212> TYPE: DNA
<213> ORGANISM: Artificial Sequence
<220> FEATURE:
<223> OTHER INFORMATION: DNA Sequence encoding the mature fusion protein
      Human 14.18 sFv (VL-VH)-Fc, with introns

<400> SEQUENCE: 8

| | |
|---|---|
| gacgtggtga tgacccagac ccccctgtcc ctgcccgtga ccccggcga gcccgcctcc | 60 |
| atctcctgca gatctagtca gagtcttgta caccgtaatg gaaacaccta tttacattgg | 120 |
| tacctgcaga agccaggcca gtctccaaag ctcctgattc acaaagtttc caaccgattt | 180 |
| tctggggtcc cagacaggtt cagtggcagt ggatcaggga cagatttcac actcaagatc | 240 |
| agcagagtgg aggctgagga tctgggagtt tatttctgtt ctcaaagtac acatgttcct | 300 |
| ccgctcacgt tcggtgctgg gaccaagctg gagctgaaat ccggaggcgg tgggtcggga | 360 |
| ggtggcgggt ctggtggtgg aggcagcggt ggtgggggat ccgaggtgca gctggtgcag | 420 |
| tccggcgccg aggtggagaa gcccggcgcc tccgtgaaga tctcctgcaa ggcctccggc | 480 |
| tcctccttca ccggctacaa catgaactgg gtgcgccaga acatcggcaa gtccctggag | 540 |
| tggatcggcg ccatcgaccc ctactacggc ggcacctcct acaaccagaa gttcaagggc | 600 |
| cgcgccaccc tgaccgtgga caagtccacc tccaccgcct acatgcacct gaagtccctg | 660 |
| cgctccgagg acaccgccgt gtactactgc gtgtccggca tggagtactg gggccagggc | 720 |
| acctccgtga ccgtgtcctc cgagcccaaa tcttgtgaca aaactcacac atgcccaccg | 780 |
| tgcccaggta gcagccca ggcctcgccc tccagctcaa ggcgggacag gtgccctaga | 840 |
| gtagcctgca tccagggaca ggccccagcc gggtgctgac acgtccacct ccatctcttc | 900 |
| ctcagcacct gaactcctgg ggggaccgtc agtcttcctc ttccccccaa acccaagga | 960 |
| caccctcatg atctcccgga cccctgaggt cacatgcgtg gtggtggacg tgagccacga | 1020 |
| agaccctgag gtcaagttca actggtacgt ggacggcgtg gaggtgcata atgccaagac | 1080 |
| aaagccgcgg gaggagcagt acaacagcac gtaccgtgtg gtcagcgtcc tcaccgtcct | 1140 |
| gcaccaggac tggctgaatg gcaaggagta caagtgcaag gtctccaaca aagccctccc | 1200 |
| agcccccatc gagaaaacca tctccaaagc caaaggtggg accgtggggg tgcgagggcc | 1260 |
| acatggacag aggccggctc ggcccaccct ctgcccgag agtgaccgct gtaccaacct | 1320 |
| ctgtccctac agggcagccc cgagaaccac aggtgtacac cctgccccca tcccgggagg | 1380 |
| agatgaccaa gaaccaggtc agcctgacct gcctggtcaa aggcttctat cccagcgaca | 1440 |
| tcgccgtgga gtgggagagc aatgggcagc cggagaacaa ctacaagacc acgcctcccg | 1500 |
| tgctggactc cgacggctcc ttcttcctct atagcaagct caccgtggac aagagcaggt | 1560 |
| ggcagcaggg gaacgtcttc tcatgctccg tgatgcatga ggctctgcac aaccactaca | 1620 |
| cgcagaagag cctctcccctg tccccgggta aatga | 1655 |

<210> SEQ ID NO 9
<211> LENGTH: 479
<212> TYPE: PRT
<213> ORGANISM: Artificial Sequence
<220> FEATURE:
<223> OTHER INFORMATION: Amino Acid Sequence of the Mature Fusion
      Protein Human 14.18 sFv (VL-VH)-Fc

<400> SEQUENCE: 9

```
Asp Val Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Arg
            20                  25                  30

Asn Gly Asn Thr Tyr Leu His Trp Tyr Leu Gln Lys Pro Gly Gln Ser
        35                  40                  45

Pro Lys Leu Leu Ile His Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Leu Thr Phe Gly Ala Gly Thr Lys Leu Glu Leu
            100                 105                 110

Lys Ser Gly Gly Gly Gly Ser Gly Gly Gly Ser Gly Gly Gly Gly
        115                 120                 125

Ser Gly Gly Gly Gly Ser Glu Val Gln Leu Val Gln Ser Gly Ala Glu
    130                 135                 140

Val Glu Lys Pro Gly Ala Ser Val Lys Ile Ser Cys Lys Ala Ser Gly
145                 150                 155                 160

Ser Ser Phe Thr Gly Tyr Asn Met Asn Trp Val Arg Gln Asn Ile Gly
                165                 170                 175

Lys Ser Leu Glu Trp Ile Gly Ala Ile Asp Pro Tyr Tyr Gly Gly Thr
            180                 185                 190

Ser Tyr Asn Gln Lys Phe Lys Gly Arg Ala Thr Leu Thr Val Asp Lys
        195                 200                 205

Ser Thr Ser Thr Ala Tyr Met His Leu Lys Ser Leu Arg Ser Glu Asp
210                 215                 220

Thr Ala Val Tyr Tyr Cys Val Ser Gly Met Glu Tyr Trp Gly Gln Gly
225                 230                 235                 240

Thr Ser Val Thr Val Ser Ser Glu Pro Lys Ser Cys Asp Lys Thr His
                245                 250                 255

Thr Cys Pro Pro Cys Pro Ala Pro Glu Leu Leu Gly Gly Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
370                 375                 380

Pro Ser Arg Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415
```

```
Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
            435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Lys
465                 470                 475

<210> SEQ ID NO 10
<211> LENGTH: 20
<212> TYPE: PRT
<213> ORGANISM: Artificial Sequence
<220> FEATURE:
<223> OTHER INFORMATION: Polypeptide linker sequence

<400> SEQUENCE: 10

Gly Gly Gly Gly Ser Gly Gly Gly Gly Ser Gly Gly Gly Gly Ser Gly
1               5                   10                  15

Gly Gly Gly Ser
            20
```

ANTI-CANCER ANTIBODIES WITH REDUCED COMPLEMENT FIXATION

RELATED APPLICATIONS

This application is a divisional of U.S. patent application Ser. No. 14/478,753, filed Sep. 5, 2014, which is a continuation of U.S. patent application Ser. No. 12/209,935, filed Sep. 12, 2008, issued as U.S. Pat. No. 8,835,606, which is a continuation of U.S. patent application Ser. No. 11/040,071, filed Jan. 21, 2005, issued as U.S. Pat. No. 7,432,357, which claims priority to and the benefit of U.S. Provisional Patent Application No. 60/538,348, filed Jan. 22, 2004, the contents of each of which are expressly incorporated by reference herein in their entireties.

FIELD OF THE INVENTION

The invention relates generally to the field of anti-cancer antibodies for targeting tumor cells. More specifically, the invention relates to anti-GD2 antibodies for targeting tumor cells expressing the glycolipid GD2.

BACKGROUND OF THE INVENTION

A common method of treating cancer involves using antibodies to attack tumor cells by specifically targeting tumor cell associated antigens. One specific example of this method involves using anti-GD2 antibodies targeted against GD2, a glycolipid which is highly expressed in certain tumor cells, such as glioblastoma, melanoma, small-cell lung carcinoma, and neuroblastoma. Specifically, anti-GD2 antibodies, such as 14.18, have been tested against neuroblastoma and osteosarcoma tumors (Yu et al., *J. Clin. Oncol.,* [1998]; 16: 2169-80), with encouraging results. However, because GD2 is also expressed in nerve endings, pain is a serious side effect of anti-GD2 antibody treatment (Kushner et al., *J. Clin. Oncol.,* [2001]; 19: 4189-94; Frost et al., *Cancer,* [1997]; 80: 317-33; Yu et al., *J. Clin. Oncol.,* [1998]; 16: 2169-80). Thus, there is a need in the art for antibodies directed against GD2 that exhibit reduced side effects, while maintaining effectiveness in treating cancers that express the GD2 glycolipid.

SUMMARY OF THE INVENTION

The invention relates to proteins comprising antibody moieties in which the proteins bind to the GD2 glycolipid and induce antibody-dependent cell-mediated cytotoxicity (ADCC), but have reduced complement fixation. When administered to patients, the antibodies and related proteins of the invention generally result in patients experiencing lower pain levels when compared to pain levels generated by administration of the corresponding proteins not modified in accordance with the invention. As a result, in some treatment modalities, patient suffering is alleviated and quality of life is improved. In other treatment modalities, the dose of the therapeutic protein of the invention is higher than the corresponding antibody-based protein without the modifications of the invention.

In one embodiment of the invention, antibody-based proteins comprising an Fc region and a variable region capable of binding GD2 are used. In a further embodiment the Fc region is derived from IgG, more specifically IgG1. In further embodiments, the antibody-based proteins of the invention may include CH1 domains and/or CL domains. However, the presence of CH1 domains or CL domains is optional and not necessary. In a further embodiment, the variable region of the antibody based protein is connected to an Fc region by a linker, more specifically a polypeptide linker. The polypeptide linker may comprise glycine and/or serine. In one embodiment, the linker has the polypeptide sequence GGGGSGGGGSGGGGSGGGGS (SEQ ID NO:10). In a further embodiment, the variable region is at least 60%, 70%, 80%, or 90% identical to the variable region of the canonical 14.18 antibody (Yu et al., *J. Clin. Oncol.,* [1998]; 16: 2169-80; U.S. Patent Application Publication No. 2003-0157054-A1).

In another class of embodiments, modifications to the antibody-based proteins of the invention that enhance antibody-dependent cell-mediated cytotoxicity (ADCC) relative to complement fixation may also be used. In a preferred embodiment, the Fc region has a modification that reduces or abolishes complement fixation, e.g., relative to levels of ADCC. In another embodiment, the Fc region of IgG1 has been modified by the mutation Lys322Ala. Other mutations that reduce complement fixation may be used, and the mutations may be amino acid substitutions as well as deletions or insertions of amino acids. In a further embodiment, the invention provides proteins with enhanced levels of bisected N-linked oligosaccharide in the Fc moiety of an anti-GD2-based protein. In a further embodiment, the invention also provides protein production methods that enhance the formation of bisected N-linked oligosaccharides in the Fc moiety of an anti-GD2-based protein. In a particular embodiment, anti-GD2 antibodies are expressed in the rat-derived cell line YB2/0, which results in antibodies having higher ADCC activity than anti-GD2 antibodies expressed from most other cell lines.

BRIEF DESCRIPTION OF THE DRAWINGS

FIG. 1 depicts the wild-type amino acid sequence of the human 14.18 IgG1 mature heavy chain (SEQ ID NO:1).

FIG. 2 depicts an amino acid sequence of the human 14.18 IgG1 mature heavy chain with a K322A mutation (SEQ ID NO:5). The substituted alanine residue at 322 is underlined.

FIG. 3 depicts the amino acid sequence of the mature human 14.18 IgG1 light chain. (SEQ ID NO:2)

FIG. 4 depicts a nucleic acid sequence (SEQ ID NO:3), with introns, encoding a human 14.18 IgG1 mature heavy chain.

FIG. 5 depicts a nucleic acid sequence (SEQ ID NO:4), with introns, encoding a human 14.18 IgG1 mature light chain.

Figure 10:
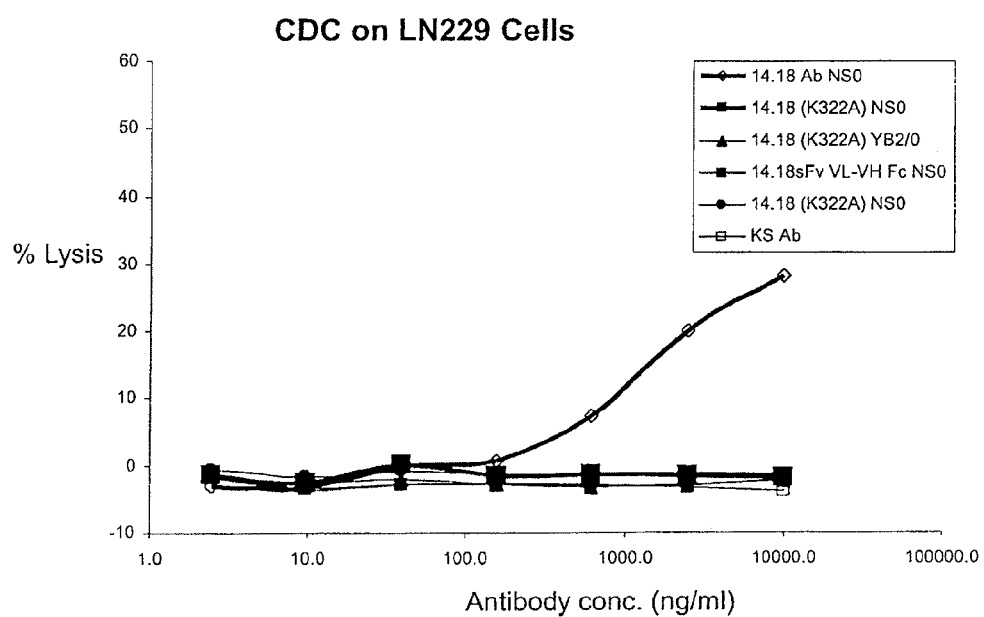

FIG. 10 depicts the results of a complement-dependent cytotoxicity assay performed on GD2 expressing LN-229 cells. The x-axis indicates the concentration of antibody in ng/ml while the y-axis indicates the percent lysis of target cells.

FIG. 11 depicts the amino acid sequence of the mature fusion protein human 14.18 sFv(VL-VH)-Fc (SEQ ID NO:9) which is an sFv antigen binding portion connected via a polypeptide linker with the amino acid sequence GGGGSGGGGSGGGGSGGGGS (SEQ ID NO:10) to an Fc fragment consisting of hinge, CH2 and CH3 domains of IgG1.

FIG. 12 depicts a nucleic acid sequence encoding the mature human 14.18 sFv(VL-VH)-Fc antibody construct (SEQ ID NO:8) of FIG. 10.

DETAILED DESCRIPTION OF THE INVENTION

The GD2 glycolipid is expressed on a variety of tumor types, but is essentially not expressed in normal tissues, with the exception of some expression at nerve endings. Antibodies directed against the GD2 glycolipid antigen have been tested in cancer patients with some success. However, presumably because of the expression of GD2 in neurons, pain is a major side effect of anti-GD2 antibody treatment, and is consequently a dose-limiting toxicity. The present invention provides anti-GD2 antibodies and related molecules that induce less pain.

As used herein, the term glycolipid GD2 or GD2 antigen is defined as a glycolipid capable of specific binding to an anti-GD2 antibody as defined herein. The term anti-GD2 antibody is defined as an antibody capable of specific binding to the antigen glycolipid GD2. As used herein, the terms "bind specifically," "specifically bind," and "specific binding" are understood to mean that the antibody has a binding affinity for a particular antigen of at least about $10^6$ $M^{-1}$, more preferably, at least about $10^7$ $M^{-1}$, more preferably at least about $10^8$ $M^{-1}$, and most preferably at least about $10^{10}$ $M^{-1}$.

As used herein, the terms "antibody" is understood to mean (i) an intact antibody (for example, a monoclonal antibody or polyclonal antibody), (ii) antigen binding portions thereof, including, for example, an Fab fragment, an Fab' fragment, an (Fab')$_2$ fragment, an Fv fragment, a single chain antibody binding site, an sFv, (iii) bi-specific antibodies and antigen binding portions thereof, and (iv) multi-specific antibodies and antigen binding portions thereof. Furthermore, the term "antibody" encompasses any of an Fab fragment, an Fab' fragment, an (Fab')$_2$ fragment, an Fv fragment, a single chain antibody binding site, or an sFv fragment linked to an Fc fragment or any portion of an Fc fragment. The linkage can be accomplished through use of linker peptide sequences known in the art. An antibody of the invention may be naturally occurring or synthetic, such as a recombinant antibody.

As used herein, the term "immunoglobulin" is understood to mean a naturally occurring or synthetically produced polypeptide homologous to an intact antibody (for example, a monoclonal antibody or polyclonal antibody) or fragment or portion thereof, such as an antigen-binding portion thereof. Immunoglobulin according to the invention may be from any class such as IgA, IgD, IgG, IgE, or IgM. IgG immunoglobulins can be of any subclass such as IgG1, IgG2, IgG3, or IgG4. The term immunoglobulin also encompasses polypeptides and fragments thereof derived from immunoglobulins. Immunoglobulins can be naturally occurring or synthetically produced, such as recombinant immunoglobulins.

The constant region of an immunoglobulin is defined as a naturally-occurring or synthetically-produced polypeptide homologous to the immunoglobulin C-terminal region, and can include a CH1 domain, a hinge, a CH2 domain, a CH3 domain, or a CH4 domain, separately or in any combination. As used herein, "Fc portion" encompasses domains derived from the constant region of an anti-GD2 antibody, including a fragment, analog, variant, mutant or derivative of the constant region. Suitable immunoglobulins include IgG1, IgG2, IgG3, IgG4, and other classes. The constant region of an immunoglobulin is defined as a naturally-occurring or synthetically-produced polypeptide homologous to the immunoglobulin C-terminal region, and can include a CH1 domain, a hinge, a CH2 domain, a CH3 domain, or a CH4 domain, separately or in any combination. In the present invention, the Fc portion typically includes at least a CH2 domain. For example, the Fc portion can include hinge-CH2-CH3. Alternatively, the Fc portion can include all or a portion of the hinge region, the CH2 domain and/or the CH3 domain and/or CH4 domain.

The term variable fragment or Fv as used herein is defined as a naturally occurring or synthetically produced polypeptide homologous to the heavy chain variable region and/or the light chain variable region. More specifically, an Fv can be an sFv or single chain variable fragment wherein the heavy chain variable region and the light chain variable region are linked together by a polypeptide moiety. Such polypeptide linker sequences are known in the art.

Anti-tumor activity of antibodies generally occurs via either complement dependent cytotoxicity (CDC or complement fixation) or through anti-body dependent cell-mediated cytotoxicity (ADCC). These two activities are known in the art as "effector functions" and are mediated by antibodies, particularly of the IgG class. All of the IgG subclasses (IgG1, IgG2, IgG3, IgG4) mediate ADCC and complement fixation to some extent, with IgG1 and IgG3 being most potent for both activities (Chapter 3, Table 3 in Paul, Essential Immunology $4^{th}$ Ed., p. 62). ADCC is believed to occur when Fc receptors on natural killer (NK) cells bind to the Fc region of antibodies bound to antigen on a cell's surface. Fc receptor binding signals the NK cell to kill the target cell. CDC is believed to occur by multiple mechanisms; one mechanism is initiated when an antibody binds to an antigen on a cell's surface. Once the antigen-antibody complex is formed, the C1q molecule is believed to bind the antigen-antibody complex. C1q then cleaves itself to initiate a cascade of enzymatic activation and cleavage of other complement proteins which then bind the target cell surface and facilitate its death through, for example, cell lysis and/or ingestion by a macrophage.

A key insight of the invention is that CDC causes the side effect of pain. Without wishing to be bound by theory, neurons may be particularly sensitive to complement fixation because this process involves the creation of channels in a cell membrane, allowing an uncontrolled ion flux. In pain-sensing neurons, even a small amount of complement fixation may be significant to generate action potentials. Thus, any amount of CDC resulting from anti-GD2 antibody binding on neurons will result in pain. According to the invention, it is advantageous to reduce complement fixation so as to reduce the level of side effects in a patient.

However, if one reduces or eliminates CDC, effective anti-tumor activity of the anti-GD2 antibody requires that levels of ADCC be maintained or even increased. A second key finding of the invention is that the antitumor activity of anti-GD2 antibodies results primarily from ADCC, and not substantially from complement fixation. Therefore, a key aspect of the invention is that it is possible to reduce or eliminate CDC function of an anti-GD2 antibody without eliminating the anti-tumor capabilities of the anti-GD2 antibody. In other words, an anti-GD2 antibody modified to reduce or eliminate complement fixation will still have anti-tumor capabilities and therefore can be effective at treating tumor growth. Consequently, the invention provides mutations in anti-GD2 antibodies that reduce complement fixation to a great extent while having a minimal effect on ADCC, such as mutation of lysine 322 to alanine (K322A) or another amino acid (Thommesen et al., *Mol. Immunol.*, [2000]; 37(16): 995-1004).

The anti-GD2 antibodies of the invention can be produced using recombinant expression vectors known in the art. The term "expression vector" refers to a replicable DNA construct used to express DNA encoding the desired anti-GD2 antibody and including a transcriptional unit of (1) genetic element(s) having a regulatory role in gene expression, for example, promoters, operators, or enhancers, operatively linked to (2) a DNA sequence encoding the desired anti-GD2 antibody which is transcribed into mRNA and translated into protein, and (3) appropriate transcription and translation initiation and termination sequences. The choice of promoter and other regulatory elements generally varies according to the intended host cell.

In a preferred example, the nucleic acid encoding the modified anti-GD2 antibody is transfected into a host cell using recombinant DNA techniques. In the context of the present invention, the foreign DNA includes a sequence encoding the inventive proteins. Suitable host cells include prokaryotic, yeast or higher eukaryotic cells.

The recombinant anti-GD2 antibodies can be expressed in yeast hosts, preferably from *Saccharomyces* species, such as *S. cerevisiae*. Yeasts of other genera such as *Pichia* or *Kluyveromyces* may also be employed. Yeast vectors will generally contain an origin of replication from a yeast plasmid or an autonomously replicating sequence (ARS), a promoter, DNA encoding the anti-GD2 antibody, as well as sequences for polyadenylation, transcription termination, and a selection gene. Suitable promoter sequences in yeast vectors include the promoters for metallothionein, 3-phosphoglycerate kinase or other glycolytic enzymes, such as enolase, glyceraldehyde-3-phosphate dehydrogenase, hexokinase, pyruvate decarboxylase, phosphofructokinase, glucose-4-phosphate isomerase, 3-phosphoglycerate mutase, pyruvate kinase, triosephosphate isomerase, phosphoglucose isomerase and glucokinase.

Various mammalian or insect cell culture systems can be employed to express the recombinant protein of the invention. Baculovirus systems for production of proteins in insect cells are well known in the art. Examples of suitable mammalian host cell lines include NS/0 cells, L cells, C127, 3T3, Chinese hamster ovary (CHO), HeLa, and BHK cell lines. Additional suitable mammalian host cells include CV-1 cells (ATCC CCL70) and COS-7 cells, both derived from monkey kidney. Another suitable monkey kidney cell line, CV-1/EBNA, was derived by transfection of the CV-1 cell line with a gene encoding Epstein-Barr virus nuclear antigen-1 (EBNA-1) and with a vector containing CMV regulatory sequences (McMahan et al., *EMBO J.*, [1991]; 10: 2821-32). The EBNA-1 gene allows for episomal replication of expression vectors, such as HAV-EO or pDC406, that contain the EBV origin of replication.

According to this invention, a particularly useful cell line for expression of anti-GD2 antibodies is the YB2/0 cell line (Shinkawa et al., *J. Biol. Chem.*, [2003]; 278: 3466-3473). Antibodies produced from this cell line have enhanced ADCC. When produced from this cell line, antibodies of the invention have a different N-linked oligosaccharide than the oligosaccharide seen in antibodies produced from other cell lines described above. Particular embodiments of the invention include anti-GD2 antibodies with non-mutant constant regions produced in YB2/0, as well as anti-GD2 antibodies with constant regions bearing mutations that reduce complement fixation, such as Lys322Ala, also produced in YB2/0 cells.

Mammalian expression vectors can include non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a poly-adenylation site, splice donor and acceptor sites, and transcriptional termination sequences. Commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence.

When secretion of the modified antibody from the host cell is desired, the expression vector can include DNA encoding signal or leader peptides, preferably placed N-terminally to both heavy and light chains. In the present invention the native signal sequences of the antibody V regions can be used, or alternatively, a heterologous signal sequence may be added, such as the signal sequence from interleukin-4.

The present invention also provides a process for preparing the recombinant proteins of the present invention including culturing a host cell transformed with an expression vector comprising a DNA sequence that encodes the anti-GD2 antibody under conditions that promote expression. The desired protein is then purified from culture media or cell extracts. For example, supernatants from expression systems that secrete recombinant protein into the culture medium can be first concentrated using a commercially available protein concentration filter, for example, an Amicon or Millipore Pellicon ultrafiltration unit. Following the concentration step, the concentrate can be applied to a suitable purification matrix, as known in the art.

An "isolated" or "purified" modified anti-GD2 antibody or biologically active portion thereof is substantially free of cellular material or other contaminating proteins from the cell or tissue source from which the modified anti-GD2 antibody is derived, or substantially free from chemical precursors or other chemicals when chemically synthesized. The language "substantially free of cellular material" includes preparations of modified anti-GD2 antibody in which the protein is separated from cellular components of the cells from which it is isolated or recombinantly produced. In one embodiment, the language "substantially free of cellular material" includes preparations of modified anti-GD2 antibody having less than about 30% (by dry weight) of non-antibody (also referred to herein as a "contaminating protein"), more preferably less than about 20% of non-antibody protein, still more preferably less than about 10% of non-antibody protein, and most preferably less than about 5% non-antibody protein. When the modified anti-GD2 antibody or biologically active portion thereof is purified from a recombinant source, it is also preferably substantially free of culture medium, i.e., culture medium represents less than about 20%, more preferably less than about 10%, and most preferably less than about 5% of the volume of the protein preparation.

The term "substantially pure modified anti-GD2 antibody" refers to a preparation in which the modified anti-GD2 antibody constitutes at least 60%, 70%, 80%, 90%, 95% or 99% of the proteins in the preparation.

Methods of Treatment Using Anti-GD2 Antibody Proteins

The modified anti-GD2 antibodies of the invention are useful in treating cancers, such as GD2-expressing cancers. Such cancers include, but are not limited to, neuroblastoma, glioblastoma, melanoma, small-cell lung carcinoma, B-cell lymphoma, renal carcinoma, retinoblastoma, and other cancers of neuroectodermal origin.

Administration

The modified anti-GD2 antibodies of the invention can be incorporated into a pharmaceutical composition suitable for administration. Such compositions typically comprise the modified anti-GD2 antibodies and a pharmaceutically-acceptable carrier. As used herein the language "pharmaceutically-acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Medicaments that contain the modified anti-GD2 antibodies of the invention can have a concentration of 0.01 to 100% (w/w), though the amount varies according to the dosage form of the medicaments.

Administration dose depends on the body weight of the patients, the seriousness of the disease, and the doctor's opinion. However, it is generally advisable to administer about 0.01 to about 10 mg/kg body weight a day, preferably about 0.02 to about 2 mg/kg/day in case of injection, and more preferably about 0.5 mg/kg/day. The dose can be administered once or several times daily according to the seriousness of the disease and the doctor's opinion.

Compositions of the invention are useful when co-administered with one or more other therapeutic agents, for example, chemotherapeutic agents that are standard treatment in cancer therapy.

EXAMPLES

Example 1

Expression of an Anti-GD2 Antibody With a Mutation That Reduced Complement Fixation An expression plasmid that expresses the heavy and light chains of the human 14.18 anti-GD2 antibody with reduced complement fixation due to mutation was constructed as follows. The expression plasmid for the 14.18 anti-GD2 antibody was pdHL7-hu14.18. pdHL7 was derived from pdHL2 (Gillies et al., *J. Immunol. Methods,* [1989]; 125: 191-202), and uses the cytomegalovirus enhancer-promoter for the transcription of both the immunoglobulin light and heavy chain genes. The K322A mutation in the CH2 region was introduced by overlapping Polymerase Chain Reactions (PCR) using pdHL7-hu14.18 plasmid DNA as template. The sequence of the forward primer was 5'-TAC AAG TGC GCT GTC TCC AAC (SEQ ID NO:6), where the underlined GCT encodes the K322A substitution, and the sequence of the reverse primer was 5'-T GTT GGA GAC AGC GCA CTT GTA (SEQ ID NO:7), where the underlined AGC is the anticodon of the introduced alanine residue. The PCR product was cloned and, after sequence confirmation, the DNA containing the K322A mutation was excised as a 190 base-pair (bp) Sac II-Nae I restriction fragment (the restriction sites Sac II and Nae I are located about 90 bp upstream and 100 bp downstream, respectively, of the K322A mutation), which was then used to replace the corresponding fragment containing the K322 wild-type in the pdHL7-hu14.18 to give pdHL7-hu14.18(K322A). The expression vector for the 14.18(K322A) antibody, pdHL7-hu14.18 (K322A), was constructed in a manner analogous to the construction of pdHL7-hu14.18. However, one skilled in the art may choose from a number of acceptable vectors to express hu14.18 K322A.

Example 2

Transfection and Expression of the Anti-GD2 Antibody

Electroporation was used to introduce the DNA encoding the anti-GD2 antibody described above into a mouse myeloma NS/0 cell line or the YB2/0 cell line. To perform electroporation, cells were grown in Dulbecco's modified Eagle's medium supplemented with 10% heat-inactivated fetal bovine serum, 2 mM glutamine and penicillin/streptomycin. About $5 \times 10^6$ cells were washed once with PBS and resuspended in 0.5 ml PBS. 10 μg of linearized plasmid DNA encoding the modified anti-GD2 antibody of Example 1 was then incubated with the cells in a Gene Pulser Cuvette (0.4 cm electrode gap, BioRad) on ice for 10 min. Electroporation was performed using a Gene Pulser (BioRad, Hercules, Calif.) with settings at 0.25 V and 500 μF. Cells were allowed to recover for 10 min on ice, after which they were resuspended in growth medium and plated onto two 96 well plates.

Stably transfected clones were selected by their growth in the presence of 100 nM methotrexate (MTX), which was added to the growth medium two days post-transfection. The cells were fed two to three more times on every third day, and MTX-resistant clones appeared in 2 to 3 weeks. Supematants from clones were assayed by anti-Fc ELISA to identify clones that produced high amounts of the anti-GD2 antibody. High producing clones were isolated and propagated in growth medium containing 100 nM MTX. Typically, a serum-free growth medium, such as H-SFM or CD medium (Life Technologies), was used.

Example 3

Biochemical Analysis of the Anti-GD2 Antibody

Routine SDS-PAGE characterization was used to assess the integrity of the modified antibodies. The modified anti-GD2 antibodies were captured on Protein A Sepharose beads (Repligen, Needham, Mass.) from the tissue culture medium into which they were secreted, and were eluted by boiling in protein sample buffer, with or without a reducing agent such as β-mercaptoethanol. The samples were separated by SDS-PAGE and the protein bands were visualized by Coomassie staining. Results from SDS-PAGE showed that the modified anti-GD2 antibody proteins analyzed were present substantially as a single band, indicating that there was not any significant amount of degradation.

Example 4

Antibody-Dependent Cell-Mediated Cytotoxicity (ADCC) and Complement-Dependent Cytotoxicity (CDC) of Antibodies of the Invention To demonstrate that the modified antibodies of the invention had the desired properties, the ability of the antibodies to mediate ADCC was examined using standard procedures, essentially as described by Idusogie et al. (*J. Immunol.*, [2000]; 164: 4178-4184). Antibodies were tested against two GD2-positive, EpCAM-negative cell lines (M-21 and LN-229) and, as a control, one GD2-negative, EpCAM-positive cell line (A431) using human PBMCs as effector cells in a standard chromium release assay. All antibodies had a human IgG1 isotype.

Figure 6:
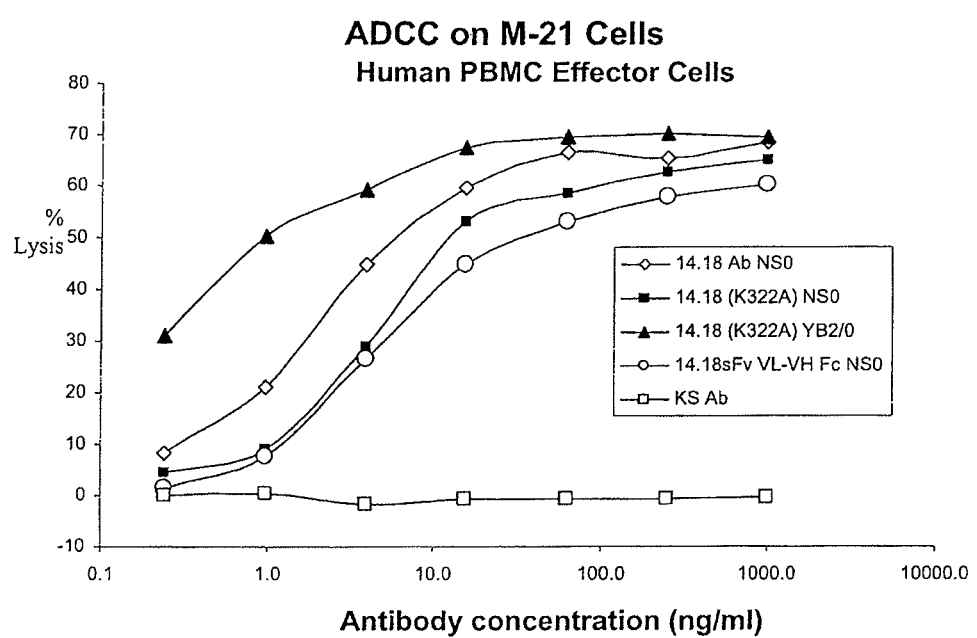
FIG. 6 depicts the results of an antibody-dependent cellular cytotoxicity assay performed on GD2 expressing M-21 cells. The x-axis indicates the concentration of antibody in ng/ml while the y-axis indicates the percent lysis of target cells.

Human IgG2 versions of 14.18 anti-GD2 antibody expressed in NS/0 cells; 14.18 with the K322A mutation, expressed in NS/0 cells; 14.18 with the K322A mutation, expressed in YB2/0 cells; and 14.18 configured as a single-chain Fv fused to an Fc, expressed in NS/0 cells; were assayed to determine their ADCC activity by measuring the percent of target M-21 cells lysed according to standard methods described previously. The KS-1/4 antibody, which does not bind target cells, was also assayed to serve as a control. As shown in FIG. 6, the K322A variant grown in YB2/0 cells had the highest overall levels of ADCC as compared to all other antibody constructs tested.

Figure 7:
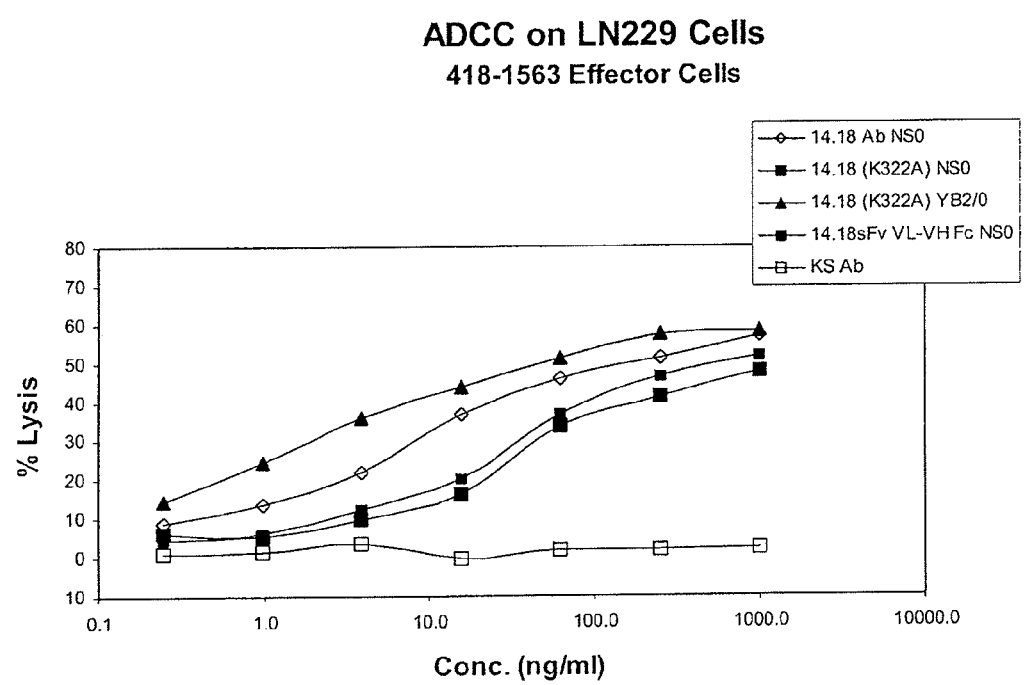
FIG. 7 depicts the results of an antibody-dependent cellular cytotoxicity assay performed on GD2 expressing LN-229 cells. The x-axis indicates the concentration of antibody in ng/ml while they-axis indicates the percent lysis of target cells.

The same constructs were also tested in a similar assay using LN-229 GD2 expressing cells as the target cells. The KS-1/4 antibody was used as a control. As shown in FIG. 7, the K322A variant grown in YB2/0 cells had the highest overall levels of ADCC as compared to all other antibody constructs tested.

Figure 8:
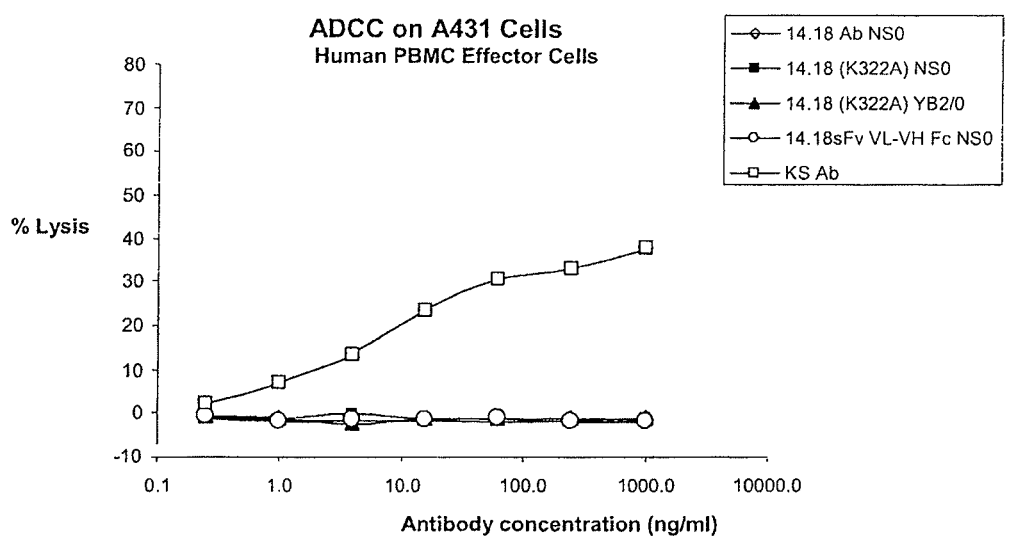
FIG. 8 depicts the results of an antibody-dependent cellular cytotoxicity assay performed on non-GD2 expressing EpCAM+ A431 cells. The x-axis indicates the concentration of antibody in ng/ml while the y-axis indicates the percent lysis of target cells.

As a control, the ADCC activity of the same anti-GD2 antibodies was tested against A431 cells which do not express the glycolipid GD2. As would be expected, the anti-GD2 antibodies showed little, if no activity, whereas the KS-1/4 antibody which is known to have ADCC activity against EpCAM expressing cells demonstrated increasing activity as concentrations of the antibody increased. (See FIG. 8). This indicates that the levels of lysis achieved in the assay of anti-GD2 antibody with M-21 cells in the previous assay need not be adjusted for any background levels of lysis activity.

In order to test the ability of anti-GD2 antibodies ability to mediate complement dependent cytotoxicity (CDC), human IgG1 versions of 14.18 expressed in NS/0 cells; two samples of 14.18 with the K322A mutation, expressed in NS/0 cells; 14.18 with the K322A mutation, expressed in YB2/0 cells; and 14.18 configured as a single-chain Fv fused to an Fc, expressed in NS/0 cells. Anti-GD2 antibodies of the invention were examined in M-21 and LN-229 cell lysis assays according to standard procedures, essentially as described by Idusogie et al. (*J. Immunol.*, [2000]; 164: 4178-4184). A 1:10 dilution of human complement was used. The KS-1/4 antibody, which does not bind to the target cells, was again used as a control.

Figure 9:
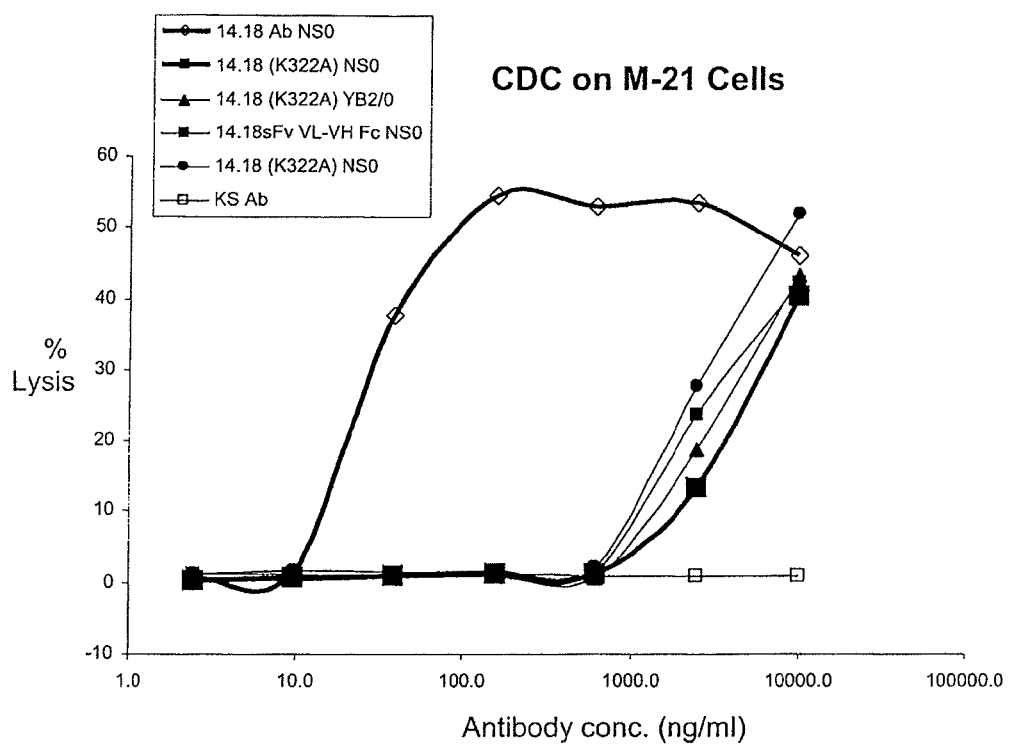
FIG. 9 depicts the results of a complement dependent cytotoxicity assay performed on GD2 expressing M-21 cells. The x-axis indicates the concentration of antibody in ng/ml while the y-axis indicates the percent lysis of target cells.

It was found that complement fixation mediated by the antibodies of the invention was profoundly reduced. As shown in FIG. 9, only 14.18 grown in NS/0 cells had levels of complement fixation at low concentrations, whereas those antibodies containing the K322A mutation exhibited little or no CDC activity at low concentrations. As shown in FIG. 10, only 14.18 anti-GD2 antibodies grown in NS/0 cells demonstrated complement fixation activity against LN229 cells, as measured by the percent of target cells lysed. The K322A variants all demonstrated little or no CDC activity at any concentration.

Taken together, the results of the ADCC and CDC assays indicate that certain modified anti-GD2 antibodies of the invention mediate ADCC, but have significantly reduced levels of complement fixation, especially as compared to typical anti-GD2 antibodies that have been used in human clinical trials.

Example 5

Treatment of Mice Bearing GD2-Expressing Tumors With Modified Anti-GD2 Antibodies To demonstrate the efficacy of the modified anti-GD2 antibodies of the invention, the modified antibody of Example 1 is tested in a mouse model of melanoma or neuroblastoma. Hu/SOD beige mice are used. The SCID and beige mutations suppress the normal mouse immune system, so that human immune cells can be added to reconstitute the immune system. Human peripheral blood mononucleocytes (PBMCs) are used. It is necessary to use human immune cells because the Fc region of human IgG1 is not recognized by murine Fc receptors to achieve ADCC.

Cells expressing GD2 are then implanted into the mice. For example, cells are implanted subcutaneously, and their growth is monitored twice per week with calipers to estimate tumor volume. As a model of neuroblastoma, the GD2-expressing cell line NXS2 is used (Greene et al., *Proc. Natl. Acad. Sci. USA*, [1975]; 72: 4923-27). As a model of melanoma, the cell line B16, modified to express GD2 is used (Haraguchi et al., *Proc. Natl. Acad. Sci. USA*, [1994]; 91: 10455-59).

Subcutaneous tumors are allowed to grow to a size of about 25 to 200 cubic millimeters, and treatment is initiated. Because the serum half-life of the modified antibodies of the invention is several days, animals are treated only one to three times per week. It is found that the volumes of tumors in mice treated with either vehicle or a control antibody increase rapidly, while the volumes of mice treated with the modified antibodies of the invention increase more slowly, or are stabilized, or in some cases shrink.

Example 6

Determination of the Maximum Tolerated Dose in a Phase I Clinical Trial

To determine the maximum tolerated dose of a modified anti-GD2 antibody of the invention, a Phase I clinical trial is performed essentially as described in Yu et al. (*J. Clin Oncol.,* [1998]; 16: 2169-80). The maximum tolerated dose of the human IgG1-based chimeric 14.18 antibody reported by Yu et al. was found to be about 20 mg/m$^2$. The maximum tolerated dose of the modified anti-GD2 antibody of the invention is found to be higher than 20 mg/m$^2$.

---

The invention claimed is:

1. A method of treating cancer, the method comprising the step of administering to a patient an anti-GD2 antibody, wherein the antibody comprises the light chain variable region of SEQ ID NO: 2, the heavy chain variable region of SEQ ID NO:1, and an Fc region with one mutation decreasing complement fixation relative to antibody-dependent, cell-mediated cytotoxicity, wherein the one mutation causes an absolute decrease in complement fixation.

2. The method of claim 1, wherein the polypeptide is administered at a dose between about 0.01 mg/kg/day and about 10 mg/kd/day.

3. The method of claim 2, wherein the dose is between about 0.02 mg/kd/day and about 2 mg/kg/day.

4. The method of claim 1, wherein the patient is a human.

5. The method of claim 1, wherein the cancer is selected from the group consisting of neuroblastoma, glioblastoma, osteosarcoma, melanoma, small-cell lung carcinoma, B-cell lymphoma, renal carcinoma, and retinoblastoma.

6. The method of claim 1, wherein the cancer is one of neuroectodermal origin.

7. The method of claim 5, wherein the cancer is neuroblastoma.

8. The method of claim 1, wherein the one mutation in the Fc region of the antibody eliminates complement fixation.

9. The method of claim 8, wherein the Fc region of the antibody is derived from IgG.

10. The method of claim 9, wherein the IgG is IgG1.

11. The method of claim 10, wherein the one mutation is a Lys322 mutation within the Fc region of human IgG1.

12. The method of claim 10, wherein the one mutation is a Lys322Ala mutation within the Fc region of human IgG1.

13. The method of claim 1, wherein the antibody further comprises a $CH_1$ domain and/or a $C_L$ domain.

14. The method of claim 1, wherein the antibody further comprises enhanced levels of bisected N-linked oligosaccharides in an Fc moiety as compared to a wild-type anti-GD2 antibody polypeptide.

15. The method of claim 1, wherein the antibody comprises the heavy chain of SEQ ID NO:1 and the light chain of SEQ ID NO:2.

* * * * *

UNITED STATES PATENT AND TRADEMARK OFFICE
CERTIFICATE OF CORRECTION

PATENT NO. : 10,017,579 B2
APPLICATION NO. : 15/483698
DATED : July 10, 2018
INVENTOR(S) : Gillies It is certified that error appears in the above-identified patent and that said Letters Patent is hereby corrected as shown below:

In the Claims

In Claim 2 at Column 25, Line 39, please delete "mg/kd/day" and replace it with -- mg/kg/day --.

In Claim 3 at Column 25, Line 41, please delete "mg/kd/day" and replace it with -- mg/kg/day --.

Signed and Sealed this
Twenty-first Day of August, 2018

Andrei Iancu
*Director of the United States Patent and Trademark Office*